United States Patent [19]

Luly et al.

[11] Patent Number: 4,826,815
[45] Date of Patent: May 2, 1989

[54] RENIN INHIBITING COMPOUNDS

[75] Inventors: Jay R. Luly, Libertyville; Joseph Dellaria, Lindenhurst; Anthony K. L. Fung, Waukegan; Dale J. Kempf, Lake Villa; Jacob J. Plattner; Saul H. Rosenberg, both of Libertyville; Hing L. Sham, Gurnee, all of Ill.

[73] Assignee: Abbott Laboratories, Abbott Park, Ill.

[21] Appl. No.: 946,881

[22] Filed: Jan. 9, 1987

Related U.S. Application Data

[63] Continuation-in-part of Ser. No. 735,491, May 17, 1985, Pat. No. 4,645,759, which is a continuation-in-part of Ser. No. 623,807, Jun. 22, 1984, abandoned.

[51] Int. Cl.$^4$ .................. A61K 37/02; C07K 5/08
[52] U.S. Cl. .................. 514/19; 514/18; 530/331; 530/338; 530/800; 564/170; 564/174; 564/180
[58] Field of Search .................. 530/331; 514/18, 19; 564/170, 174, 180, 182; 548/344, 496

[56] References Cited

U.S. PATENT DOCUMENTS 4,609,641  9/1986  Evans et al. .................. 514/18
4,645,759  2/1987  Luly et al. .................. 530/331

FOREIGN PATENT DOCUMENTS 0045665  2/1982  European Pat. Off. .............. 514/18

Primary Examiner—Delbert R. Phillips
Assistant Examiner—T. D. Wessendorf
Attorney, Agent, or Firm—Steven F. Weinstock; Steven R. Crowley; Martin L. Katz

[57] ABSTRACT

The invention relates to renin inhibiting compounds of the formula

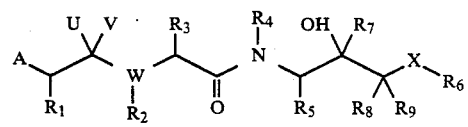

wherein A is hydrogen; loweralkyl; arylalkyl; $OR_{10}$ wherein $R_{10}$ is hydrogen or loweralkyl; $NR_{11}R_{12}$ wherein $R_{11}$ and $R_{12}$ are independently selected from hydrogen and loweralkyl; or $R_{13}$—CO—B wherein B is NH, O, $CH_2$, $HNCH_2$ and $R_{13}$ is loweralkyl, alkoxy, arylalkoxy, arylalkoxyalkyl, amino, alkylamino, dialkylamino, aminoalkyl, N-protected aminoalkyl, hydroxylated dialkylamino, (heterocyclic)alkyl or a substituted or unsubstituted heterocyclic, carboxyalkyl, or lower alkyl carboxyalkyl esters; W is N or CH: U,V may be the following combinations H,OH; OH,H; H,H; or when taken together as O represents a carbonyl with the provisos that if U,V=H,OH, then W=CH, and if U,V=O then W=N; $R_1$, $R_3$ and $R_5$ are loweralkyl or hydrophilic, lipophilic or aromatic amino acid side chains and may be the same or different; $R_2$, $R_4$, $R_7$, $R_8$ and $R_9$ are hydrogen or loweralkyl and may be the same or different; X is NH, O, S, SO, $SO_2$, or $CH_2$; and $R_6$ is loweralkyl cycloalkyl, cycloalkylalkyl, aryl, arylalkyl or an N-protecting group, with the proviso that $R_6$ may be an N-protecting group when X is NH.

17 Claims, No Drawings

RENIN INHIBITING COMPOUNDS

TECHNICAL FIELD

This application is continuation-in-part of U.S. patent application Ser. No. 735,491, filed May 17, 1985 now U.S. Pat. No. 4,645,759, which is a continuation in part of U.S. application, Ser. No. 623,807 filed June 22, 1984.

The present invention relates to novel organic compounds which inhibit renin, processes for making such compounds, synthetic intermediates employed in these processes and methods of treating hypertension with such compounds.

BACKGROUND ART

Renin is a proteolytic enzyme synthesized and stored principally in a specific part of the kidney called the juxtaglomerular apparatus. Any of three different physiologic circumstances may cause the release of renin into the circulation: (a) a decrease in the blood pressure entering or within the kidney itself; (b) a decrease in the blood volume in the body; or (c) a fall in the concentration of sodium in the distal tubules of the kidney.

When renin is released into the blood from the kidney, the renin angiotensin system is activated, leading to vasoconstriction and conservation of sodium, both of which result in increased blood pressure. The renin acts on a circulating protein, angiotensinogen, to cleave out a fragment called angiotensin I (AI). AI itself has only slight pharmacologic activity but, after additional cleavage by a second enzyme, angiotensin converting enzyme (ACE), forms the potent molecule angiotensin II (AII). The major pharmacological effects of AII are vasoconstriction and stimulation of the adrenal cortex to release aldosterone, a hormone which causes sodium retention. AII is cleaved by an aminopeptidase to form angiotensin III (AIII), which, compared to AII, is a less potent vasoconstrictor but a more potent inducer of aldosterone release.

Inhibitors of renin have been sought as agents for control of hypertension and as diagnostic agents for identification of cases of hypertension due to renin excess.

With these objectives in mind, the renin angiotension system has been modulated or manipulated, in the past, with ACE inhibitors. However, ACE acts on several substrates other than angiotensin I (AI), most notably the kinins which cause such undesirable side effects as pain, "leaky" capillaries, prostaglandin release and a variety of behavioral and neurologic effects. Further, ACE inhibition leads to the accumulation of AI. Although AI has much less vasoconstrictor activity than AII, its presence may negate some of the hypotensive effects of the blockade of AII synthesis.

Inhibition of other targets in the renin-angiotensin system such as AII with compounds such as saralasin can block AII activity, but would leave unimpaired and perhaps enhance the hypertensive effects of AIII.

On the other hand, there are no known side effects which result when renin is inhibited from acting on its substrate. Considerable research efforts have thus been carried out to develop useful inhibitors of renin. Past research efforts have been directed to renin antibodies, pepstatin, phospholipids and substrate analogs such as tetrapeptides and octapeptides to tridecapeptides. These inhibitors either demonstrate poor activity in inhibiting renin production or poor specificity for inhibiting renin only. However, Boger et al. have reported that statine-containing peptides possess potent and specific renin-inhibiting activity (Nature, Vol. 303, p. 81, 1983). In addition, Szelke and co-workers have described polypeptide analogs containing a non-peptide link (Nature, Vol. 299, p. 555, 1982) which also cause potent renin inhibition and show a high specificity for this enzyme.

DISCLOSURE OF THE INVENTION

In accordance with the present invention, there are renin inhibiting compounds of the formula

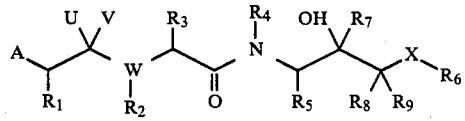

wherein A is hydrogen; loweralkyl; arylalkyl; $OR_{10}$ wherein $R_{10}$ is hydrogen or loweralkyl; $NR_{11}R_{12}$ wherein $R_{11}$ and $R_{12}$ are independently selected from hydrogen and loweralkyl; or $R_{13}$—CO—B wherein B is NH, O, $CH_2$, $HNCH_2$ and $R_{13}$ is loweralkyl, alkoxy, aryl alkoxy, arylalkoxyalkyl, amino, alkylamino, dialkylamino, aminoalkyl, N-protected aminoalyl, hydroxylated dialkylamino, (heterocyclic)alkyl or a substituted or unsubstituted heterocyclic, carboxyalkyl, or lower alkyl carboxyalkyl esters; W is N or CH; U,V may be the following combinations H,OH; OH,H; H,H; or when taken together as O represents a carbonyl group with the provisos that if U,V=H,OH, or OH,H then W=CH, and if U,V=O then W=N; $R_1$, $R_3$ and $R_5$ are loweralkyl, or hydro-philic, lipophilic or aromatic amino acid side chains and may be the same or different; $R_2$, $R_4$, $R_7$, $R_8$ and $R_9$ are hydrogen or loweralkyl and may be the same or different; X is NH, O, S, SO, $SO_2$, or $CH_2$; and $R_6$ is loweralkyl cycloalkyl, cycloalkylalkyl, aryl, arylalkyl or an N-protecting group, with the proviso that $R_6$ may be an N protecting group when X is NH.

The preferable compounds are when $R_2$, $R_4$, $R_7$, $R_8$ and $R_9$ are hydrogen, $R_1$ is benzyl, 1- or 2-naphthylmethyl and $R_5$ is isobutyl or cyclohexyl methyl. The most preferable compounds are when $R_3$ is imidazol 4 yl methyl, X is $SO_2$, or O and $R_5$ is cyclohexylmethyl.

The chiral centers of the compounds of the invention may have either the "R" or "S" configuration but preferably have an "S" configuration except where noted. The terms "S" and "R" configuration are as defined by the IUPAC 1974 Recommendations for Section E, Fundamental Stereochemistry, Pure Appl. Chem. (1976) 45, 13 30.

The term "N protecting group" or "N-protected" as used herein refers to those groups intended to protect nitrogen atoms against undesirable reactions during synthetic procedures or to prevent the attack of exopeptidases on the final compounds or to increase the solubility of the final compounds and includes but is not limited to acyl, acetyl, pivalcyl, t-butylacetyl, t-butyloxycarbonyl(Boc), benzyloxycarbonyl (Cbz) or benzoyl groups or an L- or D- aminoacyl residue, which may itself be N-protected similarly.

The term "loweralkyl" as used herein refers to straight or branched chain alkyl radicals containing from 1 to 6 carbon atoms including but not limited to methyl, ethyl, n-propyl, iso-propyl, n-butyl, iso-butyl, sec-butyl, 2-methylhexyl, n-pentyl, 1-methylbutyl, 2,2-dimethylbutyl, 2-methylpentyl, 2,2-dimethylpropyl, n-hexyl and the like.

The term "arylalkyl" as used herein refers to an unsubstituted or substituted aromatic ring appended to an alkyl radical including but not limited to benzyl, 1- and 2-naphthylmethyl, halobenzyl and alkoxybenzyl.

The term "alkylamino" as used herein refers to a loweralkyl radical appended to an NH radical.

The term "aminoalkyl" as used herein refers to —NH₂ appended to a loweralkyl radical.

The term "cycloalkyl" as used herein refers to an aliphatic ring having 4 to 7 carbon atoms.

The term "cycloalkylmethyl" as used herein refers to a cycloalkyl group appended to a methyl radical, including but not limited to cyclohexylmethyl.

The term "aryl" as used herein refers to a substituted or unsubstituted aromatic ring including but not limited to phenyl, naphthyl, halophenyl and alkoxy phenyl.

The term "alkoxy" as used herein refers to $R_{14}O—$ wherein $R_{14}$ is a loweralkyl group.

The term "arylalkoxy" as used herein refers to an aryl appended to an alkoxy radical.

The term "arylalkoxyalkyl" as used herein refers to an arylalkoxy appended to a loweralkyl radical.

The term "dialkylamino" as used herein refers to —$NR_{15}R_{16}$ wherein $R_{15}$ and $R_{16}$ are independently selected from loweralkyl groups.

The term "N-protected aminoalkyl" as used herein refers to $NHR_{17}$ is appended to a loweralkyl group, where $R_{17}$ is an N-protecting group.

The term "(heterocyclic)alkyl" as used herein refers to a heterocyclic group appended to a loweralkyl radical, including but not limited to imidazoylalkyl.

The term "heterocyclic ring" or "heterocyclic" as used herein refers to any 5-, 6-, 9- or 10-membered ring containing from one to three heteroatoms selected from the group consisting of nitrogen, oxygen, and sulfur; having various degrees of unsaturation; wherein the nitrogen and sulfur heteroatoms may optionally be quaternized; and including any bicyclic group in which any of the above heterocyclic rings is fused to a benzene ring. Heterocyclics in which nitrogen is the heteroatom are preferred. Fully saturated heterocyclics are also preferred. Preferred heterocyclics are: pyrryl, pyrrolinyl, pyrrolidinyl, pyrazolyl, pyrazolinyl, pyrazolidinyl, imidazolyl, imidazolinyl, imidazolidinyl, pyridyl, piperidinyl, pyrazinyl, piperazinyl, pyrimidinyl, pyridazinyl, oxazolyl, oxazolidinyl, isoxazolyl, isoxazolidinyl, morpholinyl, thiazolidinyl, thiazolyl, isothiazolyl, isothiazolidinyl, indolyl, quinolinyl, isoquinolinyl, benzimidazolyl, benzothiazolyl, benzoxazolyl, furyl, thienyl and benzothienyl.

Saturated heterocyclics may be unsubstituted or mono- or di- substituted with hydroxy, oxo, amino, alkylamino, dialkylamino or loweralkyl. Unsaturated heterocyclics may be unsubstituted or monosubstituted with hydroxy, amino, alkylamino, dialkylamino or loweralkyl.

The most preferred heterocyclics are as follows:

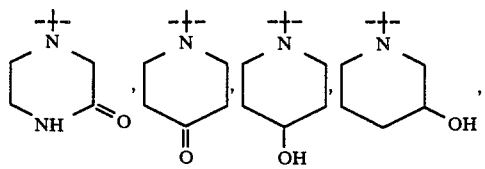

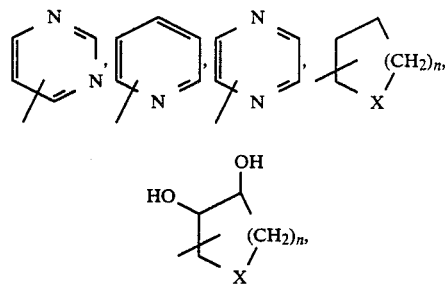

wherein n is 1 or 2 and X is N, NH, O, S, provided that X is the point of connection only when X is N,

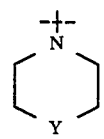

wherein Y is NH, N-loweralkyl, O, S, or SO₂, or

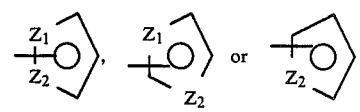

wherein $Z_1$ is N, O, or S and not the point of connection and $Z_2$ is N when it is the point of connection and NH, O or S when it is not the point of connection.

The terms "lipophilic or aromatic amino acid side chains" as used herein refer to those amino acid side chains which have an affinity for lipids or have an aromatic ring and include but are not limited to benzyl, isobutyl, isopropyl, sec-butyl, imidazol-4-yl- methyl, p-hydroxybenzyl, 1- and 2-naphthylmethyl, (pyrazolyl)methyl, (thiazolyl)methyl, and cyclohexylmethyl. The term "hydrophilic amino acid side chain" as used herein refers to those amino acid side chains which have an affinity for water and include but are not limited to, those of serine, threonine, allothreonine, homoserine, cysteine, ornithine, arginine, and glutamine. General reference to amino acid side chains in both the description and claims herein is to be taken as reference to such, whether naturally occurring in protein or not, and to both D- and L-forms.

The terms "Ala", "His", "Leu" and "Phe" as used herein refer to alanine, histidine, leucine and phenylalanine.

The following examples will serve to further illustrate preparation of novel compounds of the present invention.

EXAMPLE 1

3-t-Butyloxycarbonylamino-5-methylhex-1-ene

To a stirred suspension of methyltriphenyl phosphonium bromide (10.97 g, 30.70 mmol) in anhydrous tetrahydrofuran (200 ml) at −78° C. (dry ice/acetone bath) under an argon atmosphere, was added n-butyl lithium (19.8 ml of a 1.55 M hexane solution) dropwise over the course of 5 minutes. After 10 minutes, the −78° C. bath was replaced with a 0° C. bath for one-half hour, at which time the resulting orange solution was cooled again to −78° C. The solution was then added dropwise by cannula to a stirred −78° C. solution of Boc-leucinal (6.00 27.91 mmol) in anhydrous tetrahydrofuran (30 ml) over the course of one-half hour. The mixture was then allowed to warm to room temperature during a 3 hour period after which water (150 ml) was added. Extraction with hexane (4×100 ml) provided a combined organic phase which was washed with brine (100 ml), dried ($Na_2SO_4$), and concentrated to give crude 3-t-butyloxycabbonylamino-5-methylhex-1-ene (6.5 Chromatography with ether/hexane (1/9) provided pure 3-t-butyloxycarbonyl-amino-5-methylhex-1-ene (3.71 g, 60%). Mass spectrum: EI, $M^+ - 57 = 156$; CI, $(M+H)^+ = 214$.

EXAMPLE 2

3-t-Butyloxycarbonylamino-5-methyl 1,2-oxohexane

To a stirred solution of 3-t-butyloxycarbonyl amino-5-methylhex 1-ene (0.43 g, 2.0 mmol) in dichloromethane (20 ml) was added m-chloroperbenzoic acid (MCPBA, 1.51 g of 80% MCPBA, 7.0 mmol). After 68 hours the reaction mixture was cooled to 0° C., and 0° C. 10% $Na_2SO_3$ (5 ml) was added with stirring. After 15 minutes, the solid was filtered off and extracted with dichloromethane. The combined organic phase was washed sequentially with 0° C. 10% $Na_2SO_3$ (6 ml), saturated $NaHCO_3$ (2×6 ml), and water (5 ml). Drying ($MgSO_4$), filtering, and evaporating provided crude 3-t-butyloxycarbonylamino-5-methyl-1,2-oxohexane (0.42 g) which was chromatographed on 50 g of $SiO_2$ (hexane/ether, 3/1) to give pure 3-t-butyloxycarbonylamino 5-methyl-1,2-oxohexane (0.27 g, 59%). Mass spectrum: $M^+ = 229$.

EXAMPLE 3

3-t-Butyloxycarbonylamino-1-cyclohexyl-mercapto-2-hydroxy-5-methylhexane

To a stirred solution of 3-t-butyloxycarbonylamino 5 methyl-1,2-oxohexane (200 mg, 0.87 mmol) in methanol (8.7 ml) was added cyclohexyl mercaptan (102 mg, 0.87 mmol) and triethylamine (88 mg, 0.87 mmol). The resultant solution was refluxed for 2 hours and then evaporated to give a residue which was chromatographed on 15 of 40 μm $SiO_2$ (7/3, hexane/ether) to give 281 mg (94%) of 3-t-butyloxy-carbonylamino-1-cyclohexyl-mercapto-2 hydroxy-5-methylhexane. Mass spectrum: $M^+ = 345$.

Analysis Calcd.: C, 62.6; H, 10.2; N, 4.0.
Found: C, 62.9; H, 10.4; N, 3.9.

EXAMPLE 4

3-t-Butyloxycarbonylamino-2-hydroxy-5-methyl-1-(-phenylpropylmercapto)hexane

Using the procedure of Example 3, but replacing cyclohexyl mercaptan with 3 phenylpropyl mercaptan, gave the desired compound (93% yield). Mass spectrum: $M^+ = 381$.

Analysis Calcd: C, 66.1; H, 9.3; N, 3.7.
Found: C, 66.3; N, 9.4; H, 3.6.

EXAMPLE 5

3-t-Butyloxycarbonylamino-2-hydroxy-5 methyl-1 phenylmercaptohexane

Using the procedure of Example 3, but replacing cyclohexyl mercaptan with phenyl mercaptan, gave the desired compound (93% yield). Mass Spectrum: $M^+ = 339$.

EXAMPLE 6

3-t-Butyloxycarbonylamino-2-hydroxy 5-methyl-1β-naphthylmercaptohexane

Using the procedure of Example 3, but replacing cyclohexyl mercaptan with β-naphthyl mercaptan, gave the desired compound (65% yield). Mass spectrum: $M^+ = 389$.

EXAMPLE 7

1-Benzylmercapto-3-t-butyloxycarbonylamino-2-hydroxy-5-methylhexane

Using the procedure of Example 3, but replacing cyclohexyl mercaptan with benzyl mercaptan, gave the desired compound (57% yield) Mass spectrum: $M^+ = 353$.

EXAMPLE 8

1-p-Bromophenylmercapto-3-t-butyloxycarbonylamino-2-hydroxy-5-methylhexane

Using the procedure of Example 3, but replacing cyclohexyl mercaptan with p-bromophenyl mercaptan, gave the desired compound (71% yield). Mass spectrum: $M^+ = 418$.

EXAMPLE 9

3-t-Butyloxycarbonylamino-2-hydroxy-5-methyl-1-phenoxyhexane

To a stirred solution of 3-t-butyloxycarbonyl-amino-5-methyl-1,2-oxohexane (200 mg, 0.87 mmol) in methanol (8.7 ml) were added phenol (90 mg, 0.96 mmol) and triethylamine (97 mg, 0.96 mmol). The solution was refluxed for 44 hours and was then evaporated to give a residue which was chromatographed on 25 g of 40 μm $SiO_2$ (7/3, hexane/ether) to give 71 mg (25%) of pure 3-t-butyloxycarbonylamino 2-hydroxy-5-methyl-1phenoxyhexane. Mass spectrum: $M^+ = 323$.

EXAMPLE 10

3-t-Butyloxycarbonylamino-2-hydroxy-5-methyl-1-phenylaminohexane

To a stirred solution of 3-t-butyloxycarbonylamino 5-methyl-1,2-oxohexane (200 mg, 0.87 mmol) in methanol (10 ml) was added aniline (79 1, 0.87 mmol). The solution was refluxed for approximately 20 hours and was then evaporated to give a residue which was chromatographed on $SiO_2$ (3/2, hexane/ether) to give mg (50% of 3-t-butyloxycarbonylamino-2-hydroxy-methyl-1-phenylaminohexane). Mass spectrum: $M^+ = 323$.

EXAMPLE 11

3-Amino-1-cyclohexylmercapto-2-hydroxy-5-methylhexane hydrochloride

To a stirred solution of approximately 0.25 mmol of the resultant compound of Example 3 in methanol was added methanolic HCl (10 ml of approximately 0.75 M). After 8–12 hours, the solvent was evaporated, and the desired compound was used without further purification.

EXAMPLE 12

3-Amino-2-hydroxy-5-methyl-1-(λ-phenylpropylmercapto)hexane hydrochloride

Using the procedure of Example 11 with the resultant compound of Example 4, gave the desired compound.

EXAMPLE 13

3-Amino-2-hydroxy-5-methyl-1-phenylmercaptohexane hydrochloride

Using the procedure of Example 11 with the resultant compound of Example 5, gave the desired compound.

EXAMPLE 14

3-Amino-2-hydroxy-5 methyl-1-β-naphthylmercaptohexane hydrochloride

Using the procedure of Example 11 with the resultant compound of Example 6, gave the desired compound.

EXAMPLE 15

3-Amino-1-benzylmercapto-2-hydroxy-5-methylhexane hydrochloride

Using the procedure of Example 11 with the resultant compound of Example 7, gave the desired compound.

EXAMPLE 16

3-Amino-1-p-bromophenylmercapto-2-hydroxy-5-methylhexane hydrochloride

Using the procedure of Example 11 with the resultant compound of Example 8, gave the desired compound.

EXAMPLE 17

3-Amino-2-hydroxy-5-methyl-1-phenoxyhexane hydrochloride

Using the procedure of Example 11 with the resultant compound of Example 9, gave the desired compound.

EXAMPLE 18

3-Amino-2-hydroxy-5-methyl-1-phenylaminohexane hydrochloride

Using the procedure of Example 11 with the resultant compound of Example 10, gave the desired compound.

EXAMPLE 19

Boc-His Amide of 3-amino-1-cyclohexylmercapto-2-hydroxy-5-methylhexane

To a stirred suspension of Boc-His-OH (72 mg, 0.28 mmol) in dry dimethylformamide (3 ml) at −23° C. was added a solution of 3 amino-1-cyclohexylmercapto-2-hydroxy-5-methylhexane hydrochloride (derived from 98 mg, 0.28 mmol, of 3-t-butyloxycarbonylaminocyclohexylmercapto 2-hydroxy-5-merhylhexane using the procedure of Example 11) in dry dimethylformamide (2 ml) containing N-methylmorpholine (29 mg, 0.28 mmol). Hydroxybenzotriazole (HOBT, 58 mg, 0.43 mmol) and N,N'-dicyclohexylcarbodiimide (DCC, 59 mg, 0.28 mmol) were then added sequentially. After 2 hours the mixture was allowed to warm to room temperature. After 22 hours the mixture was filtered, evaporated, and partitioned between ethyl acetate (18 ml) and saturated NaHCO$_3$ (6 ml). The layers were separated, and the organic phase was washed with brine (5 ml), dried (Na$_2$SO$_4$), filtered, and evaporated to a solid which was chromatographed on SiO$_2$ (9/1, dichloromethane/methanol) to give 86 mg (63%) of the desired compound. Mass spectrum: (M +H)$^+$ =483.

EXAMPLE 20

Boc-His Amide of 3-amino-2-hydroxy-5-methyl-1-(-phenylpropylmercapto)hexane

Following the procedure of Example 19 but using amino-2-hydroxy-5-methyl-1-(λ-phenylpropylmercapto)-hexane hydrochloride as opposed to 3-amino-1-cyclohexylmercapto 2-hydroxy-5-methylhexane hydrochloride, gave the desired compound in 62% yield. Mass spectrum: (M +H)$^+$ =519.

Example 21

Boc-Phe-His Amide of 3-amino-1-cyclohexyl-mercapto 2-hydroxy-5-methylhexane

The resultant compound of Example 19 was treated with methanolic HCl according to the procedure used in Examples 11–18, yielding the corresponding deprotected HCl salt which was used as described below without further purification.

To a stirred 12° C. solution of Boc-Phe-OH (19.2 mg, 0.0725 mmol) in anhydrous tetrahydrofuran (3 ml) was added N-methylmrpholine (8.0 1, 0.0725 mmol) in a dropwise fashion followed by isobutylchloroformate (9.4 1, 0.0725 mmol). After 3 minutes, a −12° C. solution of the above HCl salt in anhydrous tetrahydrofuran (2 ml) containing N-methylmorpholine (16.0 1, 0.145 mmol) was added over the course of 30 seconds. After 15 minutes, the mixture was allowed to warm to room temperature for 3 hours at which time the solvent was evaporated, and the residue was partitioned between ethyl acetate (20 ml) and saturated NaHCO$_3$ (6 ml). The layers were separated and the organic phase was washed with brine (5 ml). Drying (Na$_2$SO$_4$), evaporating, and chromatographing the resulting solid on SiO$_2$ (9/1, dichloromethane/methanol) provided 11 mg of the desired compound (24% yield). Mass spectrum: (M +H)$^+$ =630.

EXAMPLE 22

Boc-Phe-His amide of 3-amino 2-hydroxy-5-methyl 1-(-phenylpropylmercapto)hexane

Using the procedure of Example 21 with the resultant compound of Example 20, instead of Example 19, gave the desired compound (18% yield). Mass spectrum: (M+H)$^+$ =666.

EXAMPLE 23

Boc-Phe-His amide of 3-amino-2 hydroxy-5-methyl 1-phenylmercaptohexane

3-Amino-2-hydroxy-5-methyl-1-phenylmercaptohexane hydrochloride was prepared from 3-t-butyloxycarbonylamino 2-hydroxy-5-methyl1-1-phenylmercaptohexane (0.610 mmol), using the procedure of Example 11, and was then partitioned between water (25 ml), brine (4 ml), and ether (10 ml). The layers were separated, and the aqueous phase was basified to pH 8 with 2 M NaOH. Extraction with chloroform (4×7 ml), drying (Na$_2$SO$_4$), and evaporating provided 91 mg (62%) of the corresponding free base (M+ =239) which was used without further purification.

To a stirred −23° C. solution of Boc-Phe-His-OH (153 mg, 0.38 mmol) in anhydrous dimethylformamide (5 ml) was added a solution of the above free base in dimethylformamide. Hydroxybenzotriazole (HOBT) and dicyclohexylcarbodiimide (DCC) were then added sequentially. After 2.5 hours, the mixture was allowed to warm to room temperature for 16 hours, at which time the mixture was filtered and evaporated to a residue which was partitioned between ethyl acetate (20 ml) and saturated NaHCO$_3$ (8 ml). The organic phase was then washed separately with saturated NaHCO$_3$ (8 ml) and brine (8 ml). Drying (Na$_2$SO$_4$) and evaporating provided a white solid which was chromatographed on SiO$_2$ (95/5, dichloromethane/methanol) to give 180 mg (75%) of the desired compound. Mass spectrum: (M +H)$^+$ =624.

EXAMPLE 24

Boc-Phe-Ala amide of 3-amino-2-hydroxy-5-methyl-1-(λ-phenylpropylmercapto)hexane To a stirred −12° C. solution of Boc-Phe-Ala-OH (47.8 mg, 0.142 mmol) in anhydrous tetrahydrofuran (3 ml) were added N-methylmorpholine (15.6 1, 0.142 mmol) and isobutylchloroformate (18.4 1, 0.142 mmol) sequentially. After 3 minutes, a −12° C. solution of the resultant compound of Example 12 (0.142 mmol) in anhydrous tetrahydrofuran (2 ml) containing N-methylmorpholine (0.142 mmol) was added. Ten minutes later, the mixture was allowed to warm to room temperature for 2 hours, at which time the solvent was evaporated, and the resulting residue was partitioned between ethyl acetate (20 ml) and saturated NaHCO$_3$ (5 ml). The organic phase was washed sequentially with 0.01 M H$_3$PO$_4$ (3 ml) and brine (5 ml). Drying (Na$_2$SO$_4$) and evaporating provided 79 mg (93%) of the desired compound. Mass spectrum: (M+H)$^+$ =600.

Analysis Calcd: C, 66.1; H, 8.2; N, 7.0.
Found: C, 65.9; H, 8.4; N, 6.9.

EXAMPLE 25

Boc-Phe-Ala amide of 3-amino-2-hydroxy-5-methyl-1 phenylmercaptohexane

Using the procedure of Example 24 with the resultant compound of Example 13, gave the desired compound. Mass spectrum: (M+H)$^+$ =558.

Analysis Calcd for: C$_{30}$H$_{43}$N$_3$O$_5$S.H$_2$O: C, 62.6; H, 7.9; N, 7.3.
Found: C, 62.6; H, 7.7; N, 7.0.

EXAMPLE 26

Boc-Phe-Ala amide of 3-amino 1-p-bromophenylmercapto-2 hydroxy-5-methylhexane

Using the procedure of Example 24 with the resultant compound of Example 16, gave the desired compound. NMR (300 MHz, CDC13, ppm): 0.9 (2d, 6H), 1.35 (d, 3H), 1.2–1.7 (m, 3H), 1.4 (s, 9H), 2.8–3.2 (m, H), 3.55–3.7 (m, 1H), 4.05 (m, 1H), 4.2–4.4 (m, 2H), 4.9 (d, 1H), 6.3–6.5 (2d, 2H), 7.15–7.45 (m, 9H).

Example 27

Boc-Phe-Ala amide of 3 amino 2-hydroxy-5-methyl-1-8-naphthylmercaptohexane

Using the procedure of Example 24 with the resultant compound of Example 14, gave the desired compound. NMR (300 MHz, CDCl$_3$, ppm): 0.9 (d, 6H), 1.35 (d, 3H), 1.2–1.7 (m, 3H), 1.4 (s, 9H), 2.9–3.3 (m, H), 3.6–3.8 (m, 1H), 4.1 (m, 1H), 4.25–4.45 (m, 2H), 4.97 (d, 1H), 6.4 (d, 2H), 7.2 (m, 2H), 7.3 (m, 3H), 7.95 (m, 3H), 7.8 (m, 4H).

EXAMPLE 28

Boc-Phe-Ala amide of 3 amino 1-benzylmercapto-2 hydroxy-5-methylhexane

Using the procedure of Example 24 with the resultant compound of Example 15, gave the desired compound. Mass spectrum: (M +H)$^+$ =572.

Analysis Calcd. for: C$_{31}$H$_{45}$N$_3$O$_5$S.½ H$_2$O: C, 64.1; H, 8.0; N, 7.2.
Found: C, 64.1; H, 7.9; N, 7.5.

EXAMPLE 29

Boc-Phe-Ala amide of 3-amino-1-cyclohexyl mercapto-2-hydroxy-5-methylhexane

Using the same procedure of Example 24 with the resultant compound of Example 11, gave the desired compound. Mass spectrum: (M +H)$^+$ =564.

EXAMPLE 30

Boc-Phe-Ala amide of 3-amino-2-hydroxy-5-methyl-1-phenoxyhexane

Using the same procedure of Example 24 with the resultant compound of Example 17, gave the desired compound. Mass spectrum: (M+H)$^+$ =542.

Analysis Calcd. for: C$_{30}$H$_{43}$N$_3$O$_6$.½ H$_2$O: C, 65.4; H, 8.0; N, 7.6.
Found: C, 65.6; H, 8.1; N, 7 6.

EXAMPLE 31

Boc-Phe-Ala amide of 3-amino-2-hydroxy-5-methyl-1-phenylaminohexane

Using the same procedure of Example 24 with the resultant compound of Example 18 (which was a dihydrochloride) rather than Example 12, and utilizing two equivalents of N-methylmorpholine, rather than one, gave the desired compound. Mass spectrum: (M +H)$^+$ =541.

Analysis Calcd. for: C$_{30}$H$_{44}$N$_4$O$_5$.½H$_2$O: C, 65.5; H, 8.2; N, 10.2.
Found: C, 65.6; H, 8.1; N, 10.0.

EXAMPLE 32

Boc-Phe-Tyr amide of 3-amino-2-hydroxy-5-methyl-1-phenylmercaptohexane

Using the procedure of Example 25 with a stirred −12° C. solution of Boc-Phe-Tyr-OH rather than Boc-Phe-Ala-OH, gave the desired compound. NMR (300 MHz, CDC13, ppm): 0.9 (m, 6H), 1.2–1.5 (m, 3H), 1.35 (s, 9H), 2.5–3.3 (m, 6H), 3.4–3.6 (m, 1H), 4.0 (m, 1H), 4.25 (m, 1H), 4.55 (m, 1H), 4.9 (m, 1H), 5.6 (br s, 1H), 6.1–6.4 (br m, 2H), 6.7 (d, 2H), 6.9 (d, 2H), 7.1–7.4 (m, 10H).

EXAMPLE 33

Boc-Phe-Phe amide of 3-amino-2-hydroxy-5-methyl-1-phenylmercaptohexane

Using the procedure of Example 25 with a stirred −12° C. solution of Boc-Phe Phe-OH rather than Boc-Phe-Ala-OH, gave the desired compound. NMR (300 MHz, CDCl$_3$, ppm): 0.9 (2d, 6H), 1.2–1.7 (m, 3H), 1.3 (s, 9H), 2.5–3.3 (m, 7H), 3.5 (m, 1H), 4.0 (m, 1H), 4.25 (m, 1H), 4.6 (m, 1H), 4.9 (br m, 1H), 6.2 (br d, 1H), 6.3 (br d, 1H), 7.0–7.4 (m, 15H).

EXAMPLE 34

2-t-Butyloxycarbonylamino-1-phenylbut-3-ene

Using the procedure of Example 1, but replacing Boc-leucinal with Boc-phenylalaninal, gave the desired compound. Mass spectrum: M+ =247.

EXAMPLE 35

2-t-Butyloxycarbonylamino-1-cyclohexylbut-3-ene

Using the procedure of Example 1, but replacing Boc-leucinal with Boc-cyclohexylalaninal, gave the desired compound. Mass spectrum: (M+H)+ =254.

Example 36

3-t-Butyloxycarbonylamino-4-phenyl-1,2-oxobutane

Using the procedure of Example 2 with the resultant compound of Example 34, gave the desired compound. Mass spectrum: (M+H)+ =264.

EXAMPLE 37

3-t-Butyloxycarbonylamino-4-cyclohexyl-1,2-oxobutane

Using the procedure of Example 2 with the resultant compound of Example 35, gave the desired compound. Mass spectrum: (M+H)+ =270.

EXAMPLE 38

3-t-Butyloxycarbonylamino-1-cyclohexylmercapto-2-hydroxy-4-phenylbutane

Using the procedure of Example 3 with the resultant compound of Example 36, gave the desired compound. Mass spectrum (M+H)+ =380.

EXAMPLE 39

3-t-Butyloxycarbonylamino-4-cyclohexyl-2-hydroxy-1-isopropylmercaptobutane

Using the procedure of Example 3 with the resultant compound of Example 37, but replacing cyclohexyl mercaptan with isopropyl mercaptan, gave the desired compound. Mass spectrum: (M+H)+ =346.

EXAMPLE 40

3-t-Butyloxycarbonylamino-4-cyclohexyl-1-cyclohexylmercapto-2-hydroxybutane

Using the procedure of Example 3 with the resultant compound of Example 37, gave the desired compound. Mass spectrum: M+ =385.

EXAMPLE 41

3-t-Butyloxycarbonylamino-4-cyclohexyl-1-cyclohexylsulfonyl-2-hydroxybutane

Treating the resultant compound of Example 40 with 2.5 equivalents of 3-chloroperoxybenzoic acid in dichloromethane, gave the desired compound after chromotography. Mass spectrum: (M+H)+ =418.

EXAMPLE 42

3-t-Butyloxycarbonylamino-1-cyclohexylsulfinyl-2-hydroxy-5-methylhexane

Treating the resultant compound of Example 3 with 1.05 equivalents of 3-chloroperoxybenzoic acid in dichloromethane, gave the desired compound after chromotography. Mass spectrum: M+ =361.

EXAMPLE 43

1-Allylmercapto-3-t-butyloxycarbonylamino-4-cyclohexyl-2-hydroxybutane

Using the procedure of Example 3 with the resultant compound of Example 37, but replacing cyclohexylmercaptan with allyl mercaptan, gave the desired compound.

EXAMPLE 44

3-Amino-1-cyclohexylmercapto-2-hydroxy-4-phenylbutane hydrochloride

Using the procedure of Example 11 with the resultant compound of Example 38, gave the desired compound.

EXAMPLE 45

3-Amino-4-cyclohexyl-2-hydroxy-1-isopropyl-mercaptobutane hydrochloride

Using the procedure of Example 11 with the resultant compound of Example 39, gave the desired compound.

EXAMPLE 46

3-Amino-4-cyclohexyl-1-cyclohexylmercapto-2-hydroxybutane hydrochloride

Using the procedure of Example 11 with the resultant compound of Example 40, gave the desired compound.

EXAMPLE 47

3-Amino 4-cyclohexyl-1-cyclohexylsulfonyl-2-hydroxybutane hydrochloride

Using the procedure of Example 11 with the resultant compound of Example 41, gave the desired compound.

EXAMPLE 48

3-Amino-1-cyclohexylsulfinyl-2-hydroxy-5-methylhexane hydrochloride

Using the procedure of Example 11 with the resultant compound of Example 42, gave the desired compound.

EXAMPLE 49

1-Allylmercapto-3-amino-4-cyclohexyl-2-hydroxybutane hydrochloride

Using the procedure of Example 11 with the resultant compound of Example 43, gave the desired compound.

EXAMPLE 50

Boc-Phe-His amide of 3-amino-1-cyclohexylmercapto-2-hydroxy-4-phenylbutane

Using the procedure of Example 23 with the resultant compound of Example 44, but replacing the free base with the amine hydrochloride and one equivalent of N-methylmorpholine, gave the desired product. Mass spectrum: (M+H)+ =664.

EXAMPLE 51

Boc-Phe-His amide of 3 amino-4-cyclohexyl-2-hydroxy-1-isopropylmercaptobutane

Using the procedure of Example 50 with the resultant compound of Example 45 gave the desired compound. Mass spectrum: (M+H)+ =630.

EXAMPLE 52

Boc-Phe-His amide of 3-amino-4-cyclohexyl-1-cyclohexylmercapto-2-hydroxybutane

Using the procedure of Example 50 with the resultant compound of Example 46 gave the desired compound. Mass spectrum: $(M+H)^+ = 670$.

EXAMPLE 53

Boc-$\beta$-Nal-His amide of 3-amino-4-cyclohexyl-1-cyclohexylmercapto-2-hydroxybutane Using the procedure of Example 50 with the resultant compound of Example 46, but replacing Boc-Phe-His with Boc-8 Naphthylalanine-His, gave the desired compound. Mass spectrum: $(M+H)^+ = 720$.

EXAMPLE 54

Boc-Phe-His amide of 3 amino-4-cyclohexyl-1-cyclohexylsulfonyl-2-hydroxybutane

Using the procedure of Example 50 with the resultant compound of Example 47 gave the desired compound.

EXAMPLE 55

Boc-Phe Ala amide of 3-amino-1-cyclohexyl sulfinyl-2-hydroxy-5-methylhexane

Using the procedure of Example 24 with the resultant compound of Example 48, gave the desired compound. Mass spectrum: $M^+ = 579$.

EXAMPLE 56

Boc-Phe-Ala amide of 1-allylmercapto-3-amino-4-cyclohexyl-2-hydroxybutane

Using the procedure of Example 24 with the resultant compound of Example 49, gave the desired compound.

EXAMPLE 57

(S)-5-Methyl-3-[(toluenesulfonyl) amino]-2-hexanone

To a stirred $-78°$ C. solution of tosyl-Leu (Ts-Leu, 3.00 g, 10.5 mmol) in dry tetrahydrofuran (THF, ml) was added 23.0 ml of a 1.39 M methyl lithium solution in ether. The mixture was warmed to room temperature for 1 hour and then poured into 55 ml of 0° C. 1M HCl. Extracting with ether, washing the combining combined extracts with saturated NaHCO$_3$ and brine, and evaporating gave 2.39 g (80%) of the desired compound. Mass spectrum: $(M+H)^+ = 284$.

EXAMPLE 58

1-t-Butyloxy-2,5-dimethyl-2-hydroxy-3-(toluenesulfonyl) aminohexane

To a $-78°$ C. solution of the resultant compound of Example 57 (1.0 g, 3.5 mmol) in dry THF (7 ml) was added 3 equivalent, of t-butoxymethyl lithium [E. J. Corey and T. M. Eckridge, Tetrahedron Letters, 3165 (1983)]. The mixture was warmed to room temperature for 4 hours and then poured into water. Acidification with 0.1 M H$_3$PO$_4$, extraction into ether, washing with brine, drying, and evaporating gave 1.1 (85%) of the desired compound. Mass spectrum: $M^+ = 371$.

EXAMPLE 59

3-Amino-1-t-butyloxy-2,5 dimethyl-2-hydroxyhexane

To a solution of the resultant compound of Example 58 (0.40 1.1 mmol) in liquid NH$_3$ (80 ml) was added sodium (0.25 g, 11 mmol) with stirring. After 5 hours the solvent was evaporated and the residue was partitioned between benzene (40 ml), ethanol (10 ml), and water (30 ml). The layers were separated and the aqueous phase was extracted with ether. The combined organic layers were dried and evaporated to give 0.19 g (79%) of the desired compound. Mass spectrum: $M^+ = 217$.

EXAMPLE 60

Boc-Phe-His amide of 3-amino-1-t-butyl oxy-2,5-dimethyl-2-hydroxyhexane

Using the procedure of Example 23 with the resultant compound of Example 59, gave the desired product.

EXAMPLE 61

4-t-Butyloxyamino-2,6-dimethylhept-2-ene

Using the procedure of Example 1, but replacing methyltriphenylphosphonium bromide with isopropyltriphenylphosphonium bromide, gave the desired compound.

EXAMPLE 62

4-Amino 2,6-dimethylhept-2-ene hydrochloride

Using the procedure of Example 11 with the resultant compound of Example 61, gave the desired compound.

EXAMPLE 63

Boc-Phe-Ala amide of 4-amino-2,6 dimethylhept-2-ene

Using the procedure of Example 24 with the resultant compound of Example 62, gave the desired compound.

EXAMPLE 64

Boc-Phe-Ala amide of 4-amino-2,6-dimethyl 2,3-oxoheptane

Using the procedure of Example 2 with the resultant compound of Example 63, gave the desired compound.

EXAMPLE 65

Boc-Phe-Ala amide of 4-amino 2,6-dimethyl 2-isobutylmercapto 3-hydroxyheptane

Using the procedure of Example 3 with the resultant compound of Example 64, but replacing cyclohexylmercaptan with isobutylmercaptan, gave the desired compound.

EXAMPLE 66

4-Cyclohexyl-1-cyclohexymercapto-2-hydroxy-3-(methylamino)butane

To a stirred suspension of lithium aluminum hydride (LAH, 4 mmol) in THF (15 ml) was added a solution of the resultant compound of Example 40 (1 mmol). The mixture was refluxed overnight, cooled, quenched sequentially with water (0.16 ml) and 3M NaOH (0.50 ml), filtered, dried, and evaporated to give the desired compound in 59% yield.

EXAMPLE 67

Boc-Phe-His amide of 4-cyclohexyl-1-cyclohexylmercapto-2 hydroxy-3-(methyl-amino)butane Using the procedure of Example 23 with the resultant compound of Example 66, gave the desired product.

EXAMPLE 68

N,N ($\alpha,\alpha$)-Methyl, t-Butyloxycarbonyl-N($\pi$)-benzyloxymethyl-L-histidine N($\alpha$)-t-Butyloxycarbonyl-N($\pi$)-benzyloxymethy-L-histidine [T. Brown, J. H. Jones, J. D. Richards, J. Chem. Soc., Perkin Trans. I, 1553 (1982)]was methylated according to a general procedure described in J. R. McDermott and N. L. Benoiton, Can. J. Chem., 1915 (1973), to give the desired product.

EXAMPLE 69

N,N($\alpha,\alpha$) Methyl, t-butyloxycarbonyl-N($\pi$)-benzyloxymethyl-L-histidine Amide of 3-Amino-cyclohexyl-1-cyclohexylmercapto-2-hydroxybutane Using the procedure of Example 19 with the resultant compound of Example 46, but replacing Boc-His with the resultant compound of Example 68, gave the desired compound.

EXAMPLE 70

N($\alpha$)-Methyl-L-histidine amide of 3-amino-cyclohexyl-1-cyclohexylmercapto-2-hydroxybutane dihydrochloride salt The resultant compound of Example 69 (100 mg) was dissolved in 1M anhydrous HCl in anhydrous methanol and was hydrogenated at 3 atmospheres $H_2$ with 30 mg of Pd black for 8h. Filtration and evaporation provided the desired compound (56 mg) which was used without further purification.

EXAMPLE 71

Boc-Phe-N($\alpha$)-methyl-L histidine amide of 3-amino-cyclohexyl-1-cyclohexylmercapto-2-hydroxybutane Using the procedure of Example 21 with the resultant compound of Example 70 and two equivalents of N-methylmorpholine, gave the desired compound.

EXAMPLE 72

3-t-Butyloxycarbonylamino-4-cyclohexyl-1-cyclohexylmethylmercapto-2-hydroxybutane Using the procedure of Example 3 with the resultant compound of Example 37, but changing cyclohexyl mercaptan to cyclohexylmethyl mercaptan, gave the desired compound in 84% yield.

EXAMPLE 73

3-Amino 4-cyclohexyl-1-cyclohexylmethylmercapto-2-hydroxybutane hydrochloride

Using the procedure of Example 11 with the resultant compound of Example 72, gave the desired compound.

EXAMPLE 74

Boc-Phe-His amide of 3-amino-4-cyclohexyl-1-cyclohexylmethylmercapto-2-hydroxybutane Using the procedure of Example 50 with the resultant compound of Example 73, gave the desired compound.

EXAMPLE 75

1-Azido-3-t-butyloxycarbonylamino-2-hydroxy -5-methylhexane

A stirred solution of the resultant compound of Example 2 (1.0 mmol) in methanol (10ml) was refluxed with sodium azide (2.4 mmol) and ammonium chloride (1.8 mmol) for 2 hours. The solvent was evaporated, and the residue was extracted with several portions of hot chloroform. The extract was filtered and evaporated to a residue which was chromatographed on $SiO_2$ eluting with hexane/ether mixtures to give the desired compound in 76% yield, mp = 50–52° C.

EXAMPLE 76

1-Amino 3-t-butyloxycarbonylamino 2-hydroxy-5 -methylhexane Hydrochloride

The resultant compound of Example 75 (400 mg) dissolved in methanol containing added $CHCl_3$ was hydrogenated over 10% Pd/C (40mg) with 3 atmospheres hydrogen. Filtration and evaporation gave the desired compound (305mg).

EXAMPLE 77

3-t-Butyloxycarbonylamino-2-hydroxy-1-(isovalerylamino)-5-methylhexane

To a solution of the resultant compound of Example 76 (1.0 mmol) and triethyl amine (2.0 mmol) in chloroform (10ml) cooled to 0° C. was added isovaleryl chloride (1.0 mmol) in $CHCl_3$ (2ml). After 3h, the solution was washed sequentially with 10% citric acid, saturated $NaHCO_3$, and brine. Drying and evaporating provided the desired compound.

EXAMPLE 78

3-Amino-2-hydroxy 1-(isovalerylamino)-5-methylhexane Hydrochloride

Using the procedure of Example 11 with the resultant compound of Example 77, gave the desired compound.

EXAMPLE 79

Boc-Phe-His Amide of 3-Amino-2-hydroxy-1-(isovalerylamino)-5-methylhexane

Using the procedure of Example 50 with the resultant compound of Example 78, gave the desired compound.

EXAMPLE 80

Boc-His Amide of 3-Amino-4-cyclohexyl-1-cyclohexylmercapto-2-hydroxybutane

Using the procedure of Example 19 employing the resultant compound of Example 46, gave the desired compound. Mass spectrum: $(M+H)^+ = 523$.

Anal. calcd. for $C_{27}H_{46}N_4O_4S$: C, 62.04; H, 8.87; N, 10.72.

Found: C, 61.72; H, 9.26; N, 10.59.

EXAMPLE 81

Dba-His Amide of 3-amino-4-cyclohexyl-1-cyclohexylmercapto-2-hydroxybutane

The compound of Example 80 was deprotected according to the method of Example 11. A solution of this material in dry dimethylformamide containing 1 equivalent of N methylmorpholine was coupled to 2,2-dibenzylacetic acid (Dba-OH) using the procedure of Example 23, to give the desired compound. Mass spectrum: $M^+ = 644$.

EXAMPLE 82

Tba-Phe-His-Amide of 3-amino-4-cyclohexyl-1-cyclohexylmercapto-2-hydroxybutane

Using the procedure of Example 81 and employing t-butylacetyl-Phe-(Tba-Phe) in lieu of DbaOH provided the desired compound. Mass spectrum: $(M+H)^+ = 668$.

EXAMPLE 83

3-t-Butyloxycarbonylamino-4-cyclohexyl-2-hydroxy-1-isopropylsulfonylbutane

Using the procedure of Example 41 employing the resultant compound of Example 39, provided the desired compound. Mass spectrum: $(M+H)^+ = 378$.

Anal. calcd. for $C_{18}H_{35}NO_5S$: 57.26; H, 9.34; N, 3.71. Found: C, 57.13; H, 9.57; N, 3.60.

EXAMPLE 84

Boc-His Amide of 3-amino 4-cyclohexyl-2-hydroxy-1-isopropylsulfonylbutane

Using the procedure of Example 19 employing the resultant compound of Example 83, provided the desired compound. Mass spectrum: $M^+ = 514$.

EXAMPLE 85

Tba-Phe-His Amide of 3-amino-4-cyclohexyl-2-hydroxy-1-isopropylsulfonylbutane

Following the procedure of Example 82 and employing the resultant compound of Example 84 in lieu of the Boc-His Amide of 3-amino-4-cyclohexylcyclohexylmercapto 2-hydrobutane provided the desired compound. Mass spectrum: $(M+H)^+ = 660$.

Anal. calcd. for $C_{36}H_{55}N_7S\frac{1}{2}H_2O$): C, 60.82; H, 7.94; N, 9.85.
Found: C, 60.70; H, 8.21; N, 9.63.

EXAMPLE 86

Dba-His Amide of 3-amino-4-cyclohexyl-2-hydroxy-1-isopropylsulfonylbutane

Using the procedure of Example 81 employing the resultant compound of Example 84, provided the desired compound. Mass spectrum: $(M+H)^+ = 637$.

EXAMPLE 87

Pp-His amide of 3-amino-4-cyclohexyl-1-cyclohexylmercapto-2-hydroxybutane

Using the procedure of Example 81, but replacing 2,2-dibenzylacetic acid with 3-phenylpropionic acid (Pp-OH), gave the desired compound.

EXAMPLE 88

Pl-His amide of 3-amino-4-cyclohexyl-1-cyclohexylmercapto-2-hydroxybutane

Using the procedure of Example 81, but replacing 2,2-dibenzylacetic acid with L-3-phenyllactic acid (Pl-OH), gave the desired compound.

EXAMPLE 89

Mpp-His amide of 3-amino-4-cyclohexyl-1-cyclohexylmercapto-2-hydroxybutane

Using the procedure of Example 81, but replacing 2,2 dibenzylacetic acid with (S)-methyl 3-phenylpropionic acid (Mpp-OH), gave the desired compound.

EXAMPLE 90

Boc-Ser amide of 3-amino-4-cyclohexyl-2-hydroxy-1-isoprpylsulfonylbutane

The resultant compound of Example 83 was treated with methanolic HCl according to Example 11 to provide the corresponding deprotected HCl salt which was used as described below without further purification.

To a stirred $-23°$ solution of Boc-Ser-OH (60 mg, 0.0291 mmol) in freshly dried dichloromethane (1 ml) were added sequentially N-methylmorpholine (33 ul, 0.0291 mmol) and isobutylchloroformate (38 ul, 0.0305 mmol)

After 5 minutes hydroxybenzotriazole (107 mg, 0.0795 mmol) was added in a single portion and the reaction stirred 15 minutes at 0° C. and cooled again to $-23°$ C. The above HCl salt and N-methylmorpholine (33 ul, 0.0305 mmol) were added as a suspension in dichloromethane (1 ml). The reaction was stirred 1 hour at $-23°$ C., 2 hours at room temperature, and partitioned between ethyl acetate and saturated $NaHCO_3$. The layers were separated and the organic phase washed sequentially with 10% HCl and brine, dried ($Na_2SO_4$) and concentrated in vacuo. The resulting film was chromatographed to provide 32 mg (26% yield) of the title compound. Mass spectrum: $(M+H)^+ = 465$.

EXAMPLE 91

Boc-Phe-Ser-amide of 3-amino 4-cyclohexyl-2-hydroxy-1-isopropylsulfonylbutane

Following the procedure of Example 21 and employing the deprotected HCl salt of Example 90 provided the title compound. Mass spectrum: $M^+ 611$.

Anal. calcd. for $C_{30}H_{49}N_3O_8S$: C,58.90; H,8.07; N,6.87. Found: C,58.86; H,8.34; N,6.53.

EXAMPLE 92

(4R)-3-(3-Phenylpropionyl)-4 (2-propyl)oxazolidine-2 one.

To a stirred solution of 4 (2-propyl)-oxazo-lidine-2-one in anhydrous tetrahydrofuran (250 mL) under a nitrogen atmosphere at $-78°$ C. were added in a dropwise fashion a solution of butyllithium in hexane (50 mL, 77.4 mmol) over 5 to 10 min. After stirring an additional 20 min at $-78°$ C. 3-phenylpropionyl chloride (12.7 mL, 85.2 mmol) was added neat. The reaction was warmed to room temperature and stirred 1 to 2 h at the temperature. The reaction was quenched by adding 100 mL of saturated aqueous ammonium chloride and the volatiles removed by rotary evaporation. The resulting aqueous residue was extracted three times with ether and the combined organic phases were washed with brine, dried ($Na_2SO_4$), filtered and concentrated in vacuo. Recrystallization from hexanes/ethyl acetate provided the title compound (16.6 g, 82%). mp =86.5 to 87.5° C. Mass spectrum: $(M+NH_4)^+=279$, $(M+H)+=262$. Mass spectrum: $(M+NH4)$

EXAMPLE 93

(4R)-3-[(2-R)-2-t-(butyl acetyl)-3-phenylpropionyl]-4-(2-propyl)-oxazolidine 2-one To a stirred solution of the product resulting from Example 92 (2.28 g, 8.72 mmol), in anhydrous tetrahydrofuran (30 mL) under a nitrogen atmosphere at −78° C. was added a solution of sodium hexamethyldisilylamide (9.6 mL, 9.59 mmol) in tetrahydrofuran. After stirring for 30 min at −78° C., t-butyl bromoacetate (2.21 g, 11.34 mmol) was added in anhydrous tetrahydrofuran and the resulting solution stirred 1 h at −78° C. The reaction was quenched by adding 20 mL of saturated aqueous ammonium chloride and partitioned between water and ether. The aqueous layer was drawn off and extracted with ether. The combined organic phases were washed with 10% aqueous HCl, saturated aqueous $NaHCO_3$, and brine, dried ($Na_2SO_4$), filtered, and concentrated in vacuo. Recrystallization from acetone/hexanes provided the desired purified product (2.59 g, 79%). mp =167°–168° C. Mass spectrum: $(M+NH_4)^+=393$, $(M+H)^+=376$.

EXAMPLE 94

Benzyl (2R)-2-(t-butyl acetyl)-3-phenylpropionate

To a stirred solution of dry benzyl alcohol (0.55 mL, 5.33 mmol) in anhydrous tetrahydro furan (18 mL) under a nitrogen atomosphere at 0° C. was added a hexane solution of n-butyllithium (2.58 mL; 4.00 mmol). To this solution was added the product from Example 93 in anhydrous tetrahydrofuran (10 mL). After stirring 1 h at 0° C. the reaction was quenched by adding excess saturated aqueous ammonium chloride. The volatiles were removed by rotary evaporation and the resulting aqueous residue extracted two times with ether. The combined organic layers were washed with brine, dried ($Na_2SO_4$),filtered, and concentrated in vacuo to provide an oil which was purified by chromatography on $SiO_2$ (15% ethyl acetate/hexane) to provide the desired product (0.89 g, 94%) as a colorless oil. Mass spectrum: $(M)^+=354$.

EXAMPLE 95

Benzyl-(2R)-2-acetyl-3-phenylpropionate

The product from Example 94 (0.52 g, 1.47 mmol) was dissolved in a 1:1 (v:v) solution (6 mL). of trifluoroacetic acid and dichloromethane and stirred at room temperature for 1 h. The volatiles were removed in vacuo to provide the title compound (0.437 g, 100%) as an oil which crystallized on standing. The unpurified material was of sufficient purity to employ in subsequent steps. Mass spectrum: $(M)+=298$.

EXAMPLE 96

Benzyl-(2R)-2 benzyl 3-(N-morpholino-carbamoyl)-propionate

The product from Example 95 (0.438 1.47 mmol), diphenylphosphoryl azide (317 uL, 1.47 mmol), and triethylamine (205 uL, 1.47 mmol) in dry benzene (6 mL) were refluxed for 3 to 5 h to provide a solution of the derived isocyanate which was cooled to 0° C. and treated with morpholine (141 uL, 1.62 mL). The cooling bath was removed and the reaction stirred for 1 h. The reaction mixture was poured into 10% aqueous HCl and extracted two times with ether. The combined organic layers were washed successively with saturated aqueous $NaHCO_3$ and brine, dried ($Na_2SO_4$), filtered and concentrated in vacuo to provide the unpurified product. The desired product (0.403 g, 72%) was obtained in pure form after chromatography on $SiO_2$ (3% methanol/chloroform) as a thick oil which formed an amorphous solid on standing. Mass spectrum: $(M)^+=382$. NMR (300 MHz, $CDCl_3$, ppm, TMS as internal standard) 7.12–7.40 (m, 10H), 5.18 (AB; J=12.6 Hz; 2H), 4.8 (dd; J=5.7, 5.7 Hz; 1H), 3.59 (d,d; J=6.0, 6.0 Hz; 4H), 3.55 (d,d,d; J=3.0, 6.0, 14.4 Hz; 1H), 3.37 (d,d,d; J=5.4, 8.4, 14.4 Hz; 1H), 3.13 (d,d; J=6.0, 6.0 Hz; 4H), 2.8–3.10 (m, 3H).

EXAMPLE 97

Benzyl-(2R) 2-benzyl-3-(ethoxycarbamoyl)-propionate

The procedure as described in Example 96 was followed except absolute ethanol was employed in lieu of morpholine. Mass spectrum: $(M)^+=341$. NMR (300 MHz, $CDCl_3$, ppm, TMS as internal standard) 7.1–7.4 (m,10H), 5.17 (s,2H), 4.96 (br s,1H), 4.07 (d,d,d; J=6.6, 6.6, 6.6 Hz,2H), 3.25–3.5 (2 br ABX,2H), 2.9–3.05 (m,2H), 2.75–2.88 (br m,1H), 1.23 (d,d; J=6.6, 6.6 Hz; 3H).

EXAMPLE 98

(2R)-2-Benzyl 3 (morpholinocarbamoyl)-propionate

The product from Example 96 (0.315 0.86 mmol) was dissolved in ethyl acetate (5 mL) and syringed into a flask charged with 10% Pd/C (0.3 g). The resulting suspension was exposed to 1 atm of gaseous hydrogen for 2 to 4 h. The catalyst was removed by filtration through a celite pad. The filtrate was concentrated in vacuo to provide the desired compound (0.21 g, 88%) as a cream colored foam which was employed without further purification. Mass spectrum: $(M+H)^+=278$.

EXAMPLE 99

(2R) 2-Benzyl-3-ethoxycarbamoylpropionate

The procedure as described in Example 98 was followed employing the product from Example 97 in lieu of that from Example 96. Mass spectrum: $(M+H)^+=252$.

EXAMPLE 100

Benzyl-(2R) 2-benzyl-3-morpholinocarbonylpropionate

The product of Example 95 was converted to the title compound using the mixed anhydride method of coupling as described in Example 21. Mass spectrum: $(M)^+=367$.

EXAMPLE 101

(2R) 2 Benzyl-3 morpholinocarbonylpropionate

The product from Example 100 was converted to the title compound following the procedure described in Example 98. Mass spectrum: $(M)^+=277$.

EXAMPLE 102

(2R) 2-Benzyl-3-(morpholinocarbonyl)propionyl-His Amide of 3-Amino-4-cyclohexyl-2-hydroxy-1-isopropylsulfonylbutane The resultant compound of Example 39 was converted to the corresponding sulfone as described in Example 41. The sulfone, 3-t Butyloxycarbonylamino-4-cyclohexyl-2-hydroxy-1-isopropylsulfonylbutane, was deprotected as described in Example 11 and converted to the Boc-His amide as described in Example 19. The Boc-His amide was deprotected in the usual fashion (Example 11) and coupled to the resultant compound of Example 101 according to the procedure of Example 19 to provide the desired compound. Mass spectrum: $(M+H)^+ = 674$.

EXAMPLE 103

(2S)-2-Benzyl-3-(ethoxycarbamoyl)-propionyl-His Amide of 3-Amino-4-cyclohexyl-2-hydroxy-1-isopropylsulfonylbutane Using the procedure of Example 102 with the resultant compound of Example 99 provided the desired compound. Mass spectrum: $(M+H)^+ = 648$.

Anal. Calcd. for $C_{32}H_{49}N_5O_7S1.5H_2O$: C, 56.95; H, 7.77; N, 10.38. Found: C, 56.99; H, 7.47; N, 10.27.

EXAMPLE 104

(2R)-2-Benzyl-3-(morpholinocarbamoyl)propionyl-His-Amide of 3 Amino-4-cyclohexyl-2-hydroxy-1-isopropylsulfonylbutane Using the procedure of Example 102 with the resultant compound of Example 98 provided the desired compound.

EXAMPLE 105

(2S,3S)-1-Azido-2-hydroxy-3-t-butyloxycarbonylamino-4-cyclohexylbutane

The resultant compound from Example 37 was treated accoding to the procedure of Example 75 to give the desired compound.

Anal. Calcd. for $C_{15}H_{28}N_4O_3$: C, 57.67; H, 9.03; N, 17.93. Found: C, 57.54; H, 9.14; N, 17.57.

EXAMPLE 106

Boc Phe-His Amide of (2S,3S)-1-Azido-2-hydroxy-3-amino-4-cyclohexylbutane.

Using the procedure of Example 50 with the resultant compound from Example 105 (which had been deprotected as described in Example 11) gave the desired compound.

Anal. Calcd. for $C_{30}H_{44}N_8O_5.H_2O$; C, 58.62; H, 7.54; N, 18.22. Found: C, 58.71; H, 7.45; N, 18.22.

EXAMPLE 107

3,3-Dimethylglutaric Acid Mono t-butyl Ester 3,3 Dimethylglutaric anhydride (455 mg, 3.2 mmol) in tetrahydrofuran (THF, 5 mL) was treated with sublimed potassium t butoxide (395 mg, 3.5 mmol). After 30 min the solution was concentrated, poured into saturated NaHCO₃ solution and washed with ether. The aqueous phase was acidified to pH 4 with 0.5M H₃PO₄ and extracted with chloroform which was dried over Na₂SO₄ and evaporated to afford 179 mg (26%) of the desired product as an oil. NMR (300 MHz, CDCl₃, ppm), 1.13 (s,6H), 1.47 (s,9H), 2.33 (s,2H), 2.45 (s,2H).

EXAMPLE 108

(4-t-Butyloxycarbonyl-3,3-dimethyl)butanoylphenylalanine benzyl Ester

Prepared according to the procedure from Example 21 from the resultant compound from Example 107 and phenylalanine benzyl ester p-toluenesulfonic acid salt. NMR (300 MHz, CDCl₃, ppm), 0.96 (s,3H), 1.00 (s,3H). 1.44 (s,9H), 1.90 (d,1H), 2.16 (d,1H), 2.25 (d,1H), 2.29 d,1H), 3.03 (dd,1H), 3.17 (dd,1H), 4.92 (m, 1H), 5.12 (d,1H), 5.16 (d,1H). 7.10–7.40 (m,10H).

EXAMPLE 109

(4-t-Butyloxycarbonyl-3,3-dimethyl)butanoyl-phenylalanine

Using the procedure of Example 98 with the resultant compound of Example 108 gave the desired product as an oil. NMR 300 MHz, CDCl₃, ppm), 0.93 (s,3H), 0.99 (s,3H), 1.45 (s,9H), 1.77 d,1H), 2.10 (d,1H), 2.19 (d,1H), 2.25 (d,1H), 3.02 (dd,1H), 3.33 (dd,1H), 4.72 (m,1H), 7.25 (m,5H).

EXAMPLE 110

(4 t-Butyloxycarbonyl-3,3-dimethyl)butanoyl-Phe-His Amide of 3-Amino-4-cyclohexyl-2 hydroxy-1-isopropylsulfonylbutane Using the procedure of Example 102 with the resultant compound from Example 109 gave the desired compound.

EXAMPLE 111

(4-Hydroxycarbonyl 3,3-dimethyl)butanoyl-Phe-His Amide of 3-Amino-4-cyclohexyl-2 hydroxy-1-isopropylsulfonylbutane The resultant compounds from Example 110 was stirred in 4M HCl/methanol or 1 h and then evaporated to provide the desired compound.

EXAMPLE 112

α-Isocyanato-L-(O-methyl)tyrosine

A suspension of (O-methyl)tyrosine methyl ester hydrochloride (6 g) in toluene (155 mL) was heated at 100° C. while phosgene was bubbled into the reaction mixture. After 2 h the mixture became homogeneous and the phosgene was continued for an additional 15 min. The mixture was cooled and evaporated with several benzene chasers to provide the desired product.

EXAMPLE 113

1-Benzyloxycarbonylamino-2,3-propanediol

1-Amino-2,3-propanediol (15.2 g, 167 mmol) and NaOH (8.1 g, 204 mmol) in water (70 mL) at −10° C. was treated dropwise with benzyl chloroformate (28.5 mL, 200 mmol) in ether (30 mL) over 20 min. The reaction was stirred at 0° C. for 30 min then at room temperature for 2 h. The mixture was acidified with 2M HCl and extracted with ethyl acetate which was wash with 0.5M H₃PO₄ and brine, then dried over Na₂SO₄ and evaporated. Recrystallization of the residue from benzene afforded 16.59 g (44%) of the desired product as a white powder. NMR (300 MHz, CD₃OD, ppm) 3.12

(dd,1H), 3.28 (dd,1H), 3.50 (m,2H), 3.68 (m,1H), 5.08 (s,2H), 7.35 (m,5H).

EXAMPLE 114

1-Methylamino-2,3-propanediol

Lithium aluminum hydride (7.20 g, 189 mmol) in tetrahdyrofuran (THF, 300 mL) was heated to reflux and the resultant compound from Example 113 (17.0 g, 75.5 mmol) in THF (150 mL) was added dropwise over 10 min. The mixture was relfuxed for 2 h, cooled, quenched sequentially with water (10 mL), 3M NaOH (40 mL) and water (20 mL), then filtered and concentrated. The residue was dissolved in water which was washed with ether and evaporated. Bulb to bulb distillation of the residue afforded 2.0 g (25%) of the desired compound as an oil. NMR (300 MHz, $CDCl_3$, ppm) 2.45 (S,3H), 2.68 dd,1H), 2.77 (dd,1H), 3.61 (dd,1H), 3.72 (dd,1H), 3.78 (M,1H).

EXAMPLE 115

(N-Methyl 2,3-dihydroxypropylamino)carbonyl(O-methyl)tyrosine methyl ester

To the resultant compound from Example 112 (1.53 g, 6.5 mmol) in dioxane (5 mL) at 0° C. was added the resultant compound from Example 114 (0.684 g, 6.5 mmol) The reaction was stirred at 0° C. for 1 h then at room temperature for 1 h, evaporated and chromatographed on silica gel with 5% methanol in chloroform to afford 1.855 g (84%) of the desired product as an oil. NMR (300 MHz, $CDCl_3$, ppm), 2.88, 2.89 (S,3H total), 3.05 (m,2H), 3.26–3.60 (m,5H), 3.73 (S,3H), 3.80 (S,3H), 4.70 (m,1H), 5.07 (broad t,1H), 6.83 (dd,1H), 7.02 (dd,1H).

EXAMPLE 116

(N-Methyl-2,3-dihydroxypropylamino)carbonyl(O-methyl)tyrosine

The resultant compound from Example 115 (114 mg, 0.355 mmol) in dioxane (4 ml) and water (2 ml) at 0° C. was treated with LiOH monohydrate (42.0 mg, 1 mmol). After 90 min 2M HCl (0.6 ml, 1.2 mmol) was added and the mixture was evaporated to a form which was used without further purification; DCI-MS: $(M+H)^+ = 327$.

EXAMPLE 117

(N-Methyl-2,3-dihydroxypropylamino)carboyl-($CH_3O$)Tyr-His Amide of 3-Amino-4-Cyclohexyl-2-hydroxy-1-isopropylsulfonylbutane Using the procedure of Example 102 with the resultant compound of Example 116 provided the desired product.

EXAMPLE 118

Boc-6-aminohexanoyl-Phe benzyl ester A mixture of 3.0 g (0.02 mol) of 6-aminohexanoic acid, 5.04 g (0.02 mol) of di-t-butyldicarbonate and 3.84 g (0.05 mol) of $NaHCO_3$ in 160 mL of 1:1 $H_2O$/tetrahydrofuran was stirred vigorously for 24 h. After concentration of the solvent, the mixture was acidified with HCl, saturated with NaCl, extracted with ethyl acetate, dried over $MgSO_4$ and concentrated in vacuo to give the desired product ($R_f$ 0.48, 9:1 chloroform/methanol).

A solution of 1.50 g (6.5 mmol) of the resultant compund from above, 2.77 (6.5 mmol) of phenylalanine benzyl ester p-toluenesulfonate salt, 0.87 g (6.5 mmol) of 1-hydroxybenzotriazole hydrate, 1.19 mL (8.4 mmol) of triethylamine and 1.74 g (8.4 mmol) of dicyclohexylcarbodiimide in 150 mL of tetrahydrofuran was allowed to stir at ambient temperature for 18 h. After concentration in vacuo, the residue was taken up in 300 mL of ethyl acetate, filtered, washed with M HCl, $H_2O$, saturated $NaHCO_3$, $H_2O$ and saturated NaCl; dried over $MgSO_4$ and concentrated. Purification by flash column chromatography gave the desired compound.

EXAMPLE 119

Boc-6-aminohexanoyl-Phe-OH

A mixture of 0.5 g (1.07 mmol) of the resultant compound of Example 118 and 30 mg of 10% palladium on carbon in 50 mL of methanol was stirred under an $H_2$ atmosphere for 3.5 h. After filtration through Celite, concentration in vacuo gave the desired compound.

EXAMPLE 120

Boc-6-aminohexanoyl-Phe-His-Amide of 3 Amino-4 cyclohexyl-2-hydroxy-1-isopropylsulfonyl butane Using the procedure of Example 102 with the resultant compound of Example 119 provided the desired compound.

EXAMPLE 121

6-Aminohexanoyl-Phe-His amide of 3-Amino4-cyclohexyl-2-hydroxy-1-isopropylsulfonyl-butane A solution of the resultant compound of Example 120 (17 mg, 0.021 mmol) in 0.2 mL of trifluoroacetic acid was allowed to stand at ambient temperature for 40 min. After removal of the solvent in vacuo, the residue was treated three times with 0.5 mL of ether and concentrated in vacuo to give the desired compound.

EXAMPLE 122

(2R,4R,5S)-2-(i-butyl)-5-(t-butyloxycarbonylamino)-4-hydroxy-6-phenylhexanoyl Amide of 3-Amino-1-cyclohexylsulfonyl-4-cyclohexyl-2-hydroxybutane Using the procedure of Evans, et.al. (J. Org. Chem. 1985, 50, 4615) with the resultant compound of Example 47 and (3R,5R,1 S)-5-(1-(t-butyloxycarbonylamino)-2-phenylethyl)-3-isobutyldihydrofuran-2-(3H)-one (D. J. Kempf, J. Org. Chem. 1986, 51, 3921) gave the desired compound

EXAMPLE 123

A. 4-t Butyloxycarbonylamino-3-hydroxy-6-methyl-1-phenylheptane

To a rapidly stirred −78° C. solution of Boc-Leucinal (1.50 g, 6.97 mmol) in anhydrous ether (10 mL) was added a −78° C. solution of phenethylmagnesium bromide (7 mmol) in anhydrous ether (40 mL) dropwise over the course of 15 min, and 45 min later the mixture was acidified. The organic phase was separated, washed with brine (2×10 mL) and dried ($Na_2SO_4$). Filtration and evaporation provided an oil (1.79 g) which was chromatographed with 150 g of 40 m$SiO_2$ (7:3, hexane:ether) to give the desired compound (0.17 g). Mass spectrum: $M^+ = 321$.

B. 4-Amino-3-hydroxy-6-methyl-1-phenylheptane hydrochloride

The resultant compound of Example A (87 mg, 0.27 mmol) was dissolved in methanol (1 mL) and was treated with methanolic HCl (5 mL of 0.75M). After 15 h the solution was evaporated to provide the desired compound as a glass (71 mg) which was used without further purification.

C. Boc-Phe-Ala amide of 4-amino-3-hydroxy-6-methyl-1-phenylheptane

To a stirred −12° C. solution of Boc-Phe-Ala-OH (91.2 mg, 0.271 mmol) in anhydrous tetrahydrofuran (5 mL) was added N-methylmorpholine (30 uL, 0.271 mmol) and isobutylchloroformate (35 uL, 0.271 mmol) sequentially. After 3 min, a −12° C. solution of 4-amino-3-hydroxy-6-methyl-1-phenylheptane hydrochloride (0.271 mmol) in anhydrous tetrahydrofuran (3 mL) containing N-methylmorpholine (0.271 mmol) was added. Ten minutes later, the mixture was allowed to warm to room temperature for 2 h, at which time the solvent was evaporated, and the resulting residue was partitioned between ethyl acetate (20 mL) and saturated $NaHCO_3$ (5 mL). The organic phase was washed sequentially with 0.01M $H_3PO_4$ (5 mL) and brine (5 mL). Drying ($Na_2SO_4$) and evaporating provided 141 mg (96%) of crude material which was chromatographed on 1.5 g of 40 mm $SiO_2$ (98/2, dichloromethane/methanol) to give 106 mg (73%) of the desired compound. NMR (300 MHz, ppm in $CDCl_3$) 0.9 (m,6H), 1.2 1.8 (m,5H), 1.35 (d,3H), 1.4 (s,9H), 2.6–3.2 (m,4H), 3.5–3.75 (m,1H), 3.95 (m,1H), 4.3 (m,1H), 4.4 (m,1H), 5.0 (m,1H), 6.5–6.7 (m,2H), 7.1–7.4 (m,5H).

EXAMPLE 124

A. 4-t Butyloxycarbonylamino-2,8-dimethyl-5-hydroxynonane

Using the procedure of Example 123A but replacing phenethyl magnesium bromide with 2 equivalents of isoamyl magnesium bromide, gave the desired compound in 60% yield.

B. 4-Amino-2,8-dimethyl-5-hydroxynonane hydrochloride

Following the procedure of Example 123B and using the resultant compound of Example 124A gave the desired compound.

C. Boc-Phe-Ala amide of 4-amino-2,8-dimethyl-5-hydroxynonane

Following the procedure of Example 123C and using the resultant compound of Example 124B, gave the desired compound.

EXAMPLE 125

Boc-Phe-His amide of 4-amino 2,8-dimethyl-5-hydroxynonane

A 250 mg portion of the product of Example 124B is partitioned between ether and 1N NaOH solution. The organic phase is dried over $NaSO_4$ and evaporated to give the free base, which is used without further purification.

To a stirred −23° C. solution of Boc-Phe-His-OH is added a solution of the above free base in dimethylformamide. Hydroxybenzotriazole (HOBT) and N',N'-dicyclohexylcarbodiimide (DCC) are then added sequentially. After 2.5 h, the mixture is allowed to warm to room temperature for 16 h, at which time the mixture is filtered and evaporated to a residue which is partitioned between ethyl acetate and saturated $NaHCO_3$. The organic phase is then washed separately with saturated $NaHCO_3$ and brine. Drying ($Na_2SO_4$) and evaporation of the solvent provides the crude product. Chromatography on $SiO_2$ eluting with dichloromethane-methanol mixtures gives the desired compound.

EXAMPLE 126

A. 5-t-Butyloxycarbonylamino-4-hydroxy-7-methyl-1-octene

Using the procedure of Example 123A but replacing phenethyl magnesium bromide with allyl magnesium bromide, gave the desired compound in 52% yield. Mass spectrum: $M^+ = 257$.

B. 5-Amino-4-hydroxy-7-methyl-1-octene hydrochloride salt

Following the procedure of Example 123B and the resultant compound of Example 126A gave the desired compound.

C. Boc-Phe-Ala amide of 5-amino-4-hydroxy-7-methyl-1-octene

Following the procedure of Example 123C and using the resultant compund of Example 126B gave the desired compound. Mass spectrum: $(M+H)^+ = 476$.

EXAMPLE 127

A. 5-t-Butyloxycarbonylamino-4-hydroxy-3,3,7-trimethyl1-octene

Using the procedure of Example 123A, but replacing phenethyl magnesium bromide with 2 equivalents of 3-methylbut-2-enyl magnesium chloride gave the desired compound in 25% yield. Mass spectrum: $M^+ = 285$.

B. 5-Amino-4-hydroxy-3,3,7-trimethyl-1-octene hydrochloride salt

Following the procedure of Example 123B and the resultant compound of Example 127A gave the desired compound.

C. Boc-Phe-Ala amide of 5-amino-4-hydroxy-3,3,7-trimethyl-1-octene

Following the procedure of Example 123C and the resultant compound of Example 127B gave the desired compound in 89% yield. Mass spectrum: M+ =503.

EXAMPLE 128

A. 2-t-Butyloxycarbonylamino-1-cyclohexyl-3-hydroxy-6-methylheptane

Following the procedure of Example 124A, but replacing Boc leucinal with Boc-cyclohexylalanal, gave the desired compound in 29% yield after chromatography. Mass spectrum: M+ =327.

B. 2-Amino-1-cyclohexyl-3-hydroxy-6-methylheptane hydrochloride salt

Following the procedure of Example 123B and using the resultant compound of Example 125A, gave the desired compound.

C. Boc Phe-His Amide of 2-Amino-1-cyclohexyl-3-hydroxy-6-methylheptane

Following the procedure of Example 125, but replacing the free base with the resultant compound of Example 128B and 1 equivalent of N-methylmorpholine, gave the desired compound in 63% yield after chromatography. Mass spectrum: M+ =611.

EXAMPLE 129

A. 1-Cyclohexyl-3-hydroxy-6-methyl-2-(methylamino)-heptane

To a stirred suspension of lithium aluminum hydride (LAH, 4 mmol) in tetrahydrofuran (THF, 15 mL) was added a solution of the resultant compound of Example 128A (1 mmol). The mixture was refluxed overnight, cooled, quenched sequentially with water (0.16 mL) and 3M NaOH (0.50 mL), filtered, dried, and evaporated to give the desired compound in 61% yield. Mass spectrum: M+ =241.

B. Boc Phe-His amide of 1-cyclohexyl-3-hydroxy-6-methyl-2-(methylamino)heptane Following the procedure of Example 125 using the resultant compound of Example 129A gave the desired compound in 63% yield. Mass spectrum: M+ =625.

EXAMPLE 130

A. N,N (α,α)-Methyl,t-butyloxycarbonyl-N(π)-benzyloxymethyl-L-histidine

N(α)-t-Butyloxycarbonyl-N(π)-benzyloxymethyl-L-histidine (T. Brown, J. H. Jones, J. D. Richards, *J. Chem. Soc. Perkin Trans* I, 1553 (1982)] was methylated according to the general procedure in J. R. McDermott and N. L. Benoiton, *Can. J. Chem.*, 1915 (1973), to give the desired product.

B. N,N(α,α)-Methyl, t-butyloxycarbonyl-N(π)-benzyloxymethyl-L-histidine amide of 2-aminocyclohexyl-3-hydroxy-6-methylheptane Following the procedure of Example 128C, but replacing Boc-Phe-His with the resultant compound of Example 130A gave the desired compound.

C. N(α)-Methyl-L-Histidine amide of 2-amino-1-cyclohexyl-3-hydroxy-6 methylheptane dihydrochloride salt The resultant compound of Example 130B (100 mg) was dissolved in 1M anhydrous HCl in anhydrous methanol and was hydrogenated at 3 atm H₂ with 30 mg of Pd black for 8 h. Filtration and evaporation provided the desired compound (63 mg) which was used without further purification.

D. Boc-Phe-N(α) methyl-L-His amide of 2-amino-1-cyclohexyl-3-hydroxy-6-methylhepane Following the procedure of Example 125 but replacing Boc-Phe-His with Boc-Phe and using the resultant compound of Example 130C with 2 equivalents of N-methylmorpholine, gave the desired compound. Mass spectrum: M+ =625.

EXAMPLE 131

2-t-Butyloxycarbonylamino-1,5-dicyclohexyl-3-hydroxypentane

Following the procedure of Example 128A but replacing isoamylmagnesium bromide with cyclohexylethylnesium bromide, gave the desired compound.

EXAMPLE 132

A. 2-Amino-1,5-dicyclohexyl-3-hydroxypentane hydrochloride salt

Following the procedure of Example 123B and using the resultant compound of Example 131 gave the desired compound.

B. Boc-α-Nal His amide of 2-amino 1,5 dicyclohexyl-3-hydroxypentane

Following the procedure of Example 125, but replacing the free base with the resultant compound of Example 132A and 1 equivalent of N methylmorpholine and replacing Boc-Phe His with Boc-α-Naphthylalanine-His, gave the desired compound.

EXAMPLE 133

A. 2-t-Butyloxycarbonylamino-1,6-dicyclohexyl-3-hydroxyhexane

Following the procedure of Example 128A but replacing isoamyl magnesium bromide with cyclohexylpropylmagnesium bromide, gave the desired compound.

B. 2 Amino-1,6-dicyclohexyl 3-hydroxyhexane hydrochloride salt

Following the procedure of Example 123B and using the resultant compound of Example 133A gave the desired compound.

C. Boc-Phe-His amide of 2 amino 1,6-dicyclohexyl-3-hydroxyhexane

Following the procedure of Exaple 125 but replacing the free base with the resultant compound of Example 133B and equivalent of N-methylmorpholine, gave the desired compound.

EXAMPLE 134

A. 2-t-Butyloxycarbonylamino-1-cyclohexyl-3-hydroxy-6-phenylhexane

Following the procedure of Example 128A but replacing isoamyl magnesium bromide with phenylpropyl magnesium bromide, gave the desired compound.

B. 2-Amino-1-cyclohexyl-3-hydroxy-6-phenylhexane hydrochloride salt

Following the procedure of Example 123B and using the resultant compound of Example 134A gave the desired compound.

C. Boc-Phe-His amide of 2-amino-1-cyclohecxyl-3-hydroxy-6-phenylhexane

Following the procedure of Example 125, but replacing the free base with the resultant compound of Example 133B and 1 equivalent of N-methylmorpholine, gave the desired compound.

EXAMPLE 135

A. Boc-His amide of 2-amino-1-cyclohexyl-3-hydroxy-6-methylheptane

Using the procedure of Example 128C, but replacing Boc-Phe-His with Boc-His gave the desired compound.

B. Dba-His amide of 2-amino 1-cyclohexyl-3-hydroxy-6-methylheptane

Using the procedure of Example 123B on the resultant compound of Example 135A, gave the corresponding deprotected material which was coupled with 2,2-dibenzylacetic acid (Dba-OH) using the method of Example 128C to give the desired material.

EXAMPLE 136

Tba Phe-His amide of 2-amino 1-cyclohexyl-3 hydroxy-6-methylheptane

Using the procedure of Example 135, but replacing 2,2-dibenzylacetic acid with t-butylacetyl-Phe (Tba-Phe), gave the desired material.

EXAMPLE 137

Pp-His amide of 2-amino-1-cyclohexyl-3-hydroxy-6-methylheptane

Using the procedure of Example 135B, but replacing 2,2-dibenzyl acetic acid with 3-phenylpropionic acid (Pp-OH) gave the desired compound.

EXAMPLE 138

Pl-His amide of 2-amino-1-cyclohexyl-3-hydroxy-6-methylheptane

Using the procedure of Example 135B, but replacing 2,2-dibenzylacetic acid with L-3-phenyllactic acid (Pl-OH), gave the desired compound.

EXAMPLE 139

Mpp-His amide of 2-amino-1-cyclohexyl-3 hydroxy-6-methylheptane

Using the procedure of Example 135B but replacing 2,2-dibenzyl acetic acid with 2(S)-methyl-3-phenylpropionic acid (Mpp-OH), gave the desired compound.

EXAMPLE 140

Boc-Ser amide of 2-amino-1-cyclohexyl-3-hydroxy-6-methylheptane

Following the procedure of 123C and replacing the free base with the resultant compound of Example 128B and employing Boc-Ser-OH in lieu of Boc-Phe-Ala-OH provided the desired compound. Mass spectrum: $M^+ = 414$.

EXAMPLE 141

Boc-Phe-Ser amide of 2-amino-1-cyclohexyl-3-hydroxy-6-methylheptane

Using the procedure of Example 123B and using the resultant compound of Example 140 gave the corresponding deprotected salt which was used without further purification. Following the procedure of Example 123 but replacing the free base with the above salt and replacing Boc-Phe Ala-OH with Boc-Phe-OH gave the desired compound. Mass spectrum: $M^+ = 561$.

EXAMPLE 142

2-t-Butyloxycarbonylamino-1-cyclohexyl-3 hydroxy-6-methylheptane

To a stirred −78° C. solution of L-Boc-cyclohexylalaninal (1.0 g, 3.9 mmol) in anhydrous tetrahydrofuran (THF, 25 mL) was added isoamyl magnesium bromide (24.4 mL of 0.8M solution in THF) dropwise over the course of 5 min. The mixture was warmed to 0° C. for 2 h and then quenched with NH$_4$Cl (1.34 25 mmol) in H$_2$O (25 mL). The THF was evaporated and the aqueous phase was extracted with ether (3×40 mL). The combined organic phase was washed (brine), dried (Na$_2$SO$_4$), evaporated, and chromatographed on silica gel eluting with ethyl acetate/hexane (15/85). Combination of selected fractions provided the less polar "S"-hydroxy diastereomer (375 mg, 29%). Mass spectrum: $M^+ = 327$.

EXAMPLE 143

Boc-Phe-His Amide of 2-Amino-1-cyclohexyl-3-hydroxy-6-methylheptane

The resultant compound of Example 142 (320 mg, 0.977 mmol) was dissolved in 25 mL of anhydrous 1M HCl in methanol. After 12 h, evaporation of the solvent provided the corresponding deprotected amine hydrochloride (241 mg, 93%) which was used in the below coupling without further purification.

To a stirred 23° C. solution of Boc-Phe-His-OH (82.4 mg) was added a solution of the above amine salt (54 mg) in dimethylformamide. Hydroxybenzotriazole (HOBT, 41.5 mg) N-methylmorpholine (21 mg), and N′,N′-dicyclohexylcarbodiimide (DCC, 42.2 mg) were then added sequentially. After 2.5 h, the mixture was allowed to warm to room temperature for 16 h, at which time the mixture was filtered and evaporated to a residue which was partitioned between ethyl acetate and saturated NaHCO$_3$. The organic phase was then washed separately with saturated NaHCO$_3$ and brine.

Drying (Na$_2$SO$_4$) and evaporation of the solvent provided the crude product. Chromatography on SiO$_2$ eluting with dichloromethane-methanol mixtures gave the desired compound (79 mg, 63%). Mass spectrum: M$^+$=611.

EXAMPLE 144

Boc-His-Amide of 2-Amino-1 cyclohexyl-3-hydroxy-6-methylheptane

Following the procedure of Example 143, but replacing Boc-Phe-His-OH with Boc-His-OH, gave the desired compound in 47% yield.

EXAMPLE 145

Cbz-D-Ala Phe-His Amide of 2-Amino-1-cyclohexyl-3-hydroxy-6-methylheptane

Following the procedure of Example 143, but replacing Boc-Phe-His OH with Cbz-D-Ala-Phe-OH and replacing the resultant compound of Example 142 with the resultant compound of Example 144 gave the desired product.

EXAMPLE 146

D-Ala-Phe-His Amide of 2-Amino-1-cyclohexyl-3-hydroxy-6-methylheptane

The resultant compound of Example 145 (1.0 in glacial acetic acid (20 mL) was hydrogenated with 10% Pd/C (450 mg) at 55 p.s.i. H$_2$. After 3 h, the mixture was filtered and evaporated. The residue was partitioned between ethyl acetate and saturated aqueous NaHCO$_3$ for 30 min. The organic phase was washed (brine), dried (Na$_2$SO$_4$), filtered, and evaporated to give the desired compound in 84% yield.

EXAMPLE 147

D-Ser-Phe-His Amide of 2-Amino-1-cyclohexyl-3 hydroxy-6-methylheptane

Following the procedures of Examples 145 and 146, but replacing Cbz-D-Ala-Phe-OH with Cbz-D-Ser-Phe-OH, gave the desired product in 39% yield.

EXAMPLE 148

(OCH$_3$)Tyr-His Amide of 2-Amino-1-cyclohexyl-3-hydroxy-6-methylheptane

Following the procedures of Examples 145 and 146, but replacing Cbz-D-Ala-Phe-OH with Cbz-(OCH$_3$)Tyr, gave the desired product.

EXAMPLE 149

(Imidazol-4-yl)acetyl-(OCH$_3$)Tyr-His Amide of 2-Amino-1-cyclohexyl-3-hydroxy-6-methylheptane Following the procedure of Example 143, but replacing Boc-Phe-His-OH with (imidazol-4-yl)acetic acid, and replacing the salt derived from the resultant compound of Example 142 with the resultant compound of Example 148, gave the desired compound in 34% yield after recrystallization.

EXAMPLE 150

(Imidazol-1-yl)acetyl-(OCH$_3$)Tyr-His Amide of 2-Amino-1-cyclohexyl-3-hydroxy-6-methylheptane The resultant compound of Example 148 (250 mg) in dry THF at 0° C. was treated sequentially with 2 eq. N-methylmorpholine and 1 eq bromoacetyl bromide. After 1 h, imidazole (5 eq) was added. The mixture was warmed to room temperature for 6 h and then evaporated. Chromatography of the residue on silica gel (dichloromethane/isopropylamine/methanol, 89:9:2) provided the desired product.

EXAMPLE 151

N-(2,3-dihydroxypropyl)Gly-(OCH$_3$)Tyr-His Amide of 2-Amino-1-cyclohexyl-3-hydroxy-6-methylheptane Following the procedure of Example 150, but replacing imidazole with 1-amino-2,3-dihydroxypropane provided the desired product.

EXAMPLE 152

3-Benzyloxycarbonylamino-3-methylbutanoic Acid

A solution of 2,2-dimethyl-3-carbomethyoxypropionic acid [LeMaul, *Bull. Soc. Chim. Fr.*, 828 (1965), 20 g, 0.125 mol], diphenylphosphorylazide (34.3 g, 0.125 mol) and triethylamine was heated in toluene (150 mL) at 100° C. for 2 h. After cooling to 5° C., the toluene solution was washed successively with 0.5M HCl, aqueous NaHCO$_3$ and brine. Evaporation of the dried solution gave a residue which was chromatographed on silica gel eluting with 60/40 hexane-ether. There was obtained 13 g of methyl 3-isocyanato-3-methylbutanoate as a mobile liquid. A solution of this material in toluene (20 mL) was treated with benzyl alcohol (13 mL) and the resulting mixture heated at reflux for 40 h. Evaporation of the toluene left a residue which was dissolved in methanol (125 mL) and then treated with a solution of NaOH (6.6 g, 0.165 mol) in 22 mL of water. After 5 h, the reaction mixture was partially evaporated, washed with ether and acidified with 6N HCl. Extraction with methylene chloride and evaporation gave 21 g of the desired product. NMR (300 MHz, CDCl$_3$): 1.42 (s,6H), 2.78 (s,2H), 5.08 (s,2H).

EXAMPLE 153

Cbz-[(β,β-di-Me)-β-Ala]-Phe-OCH$_3$

A 4.0 g sample of 3-benzyloxycarbonylamino-3-methylbutanoic acid was coupled to phenylalanine methyl ester hydrochloride (3.43 g) using the mixed anhydride procedure described in Example 123C. Purification of the crude product by flash chromatography eluting with 65/35 ether/hexane gave an 86% yield of product. NMR (300 MHz, CDCl$_3$): 1.32 (s,3H), 1.34 (s,3H), 2.46 (d,1H), 2.63 (d,1H), 2.98 (dd,1H), 3.09 (dd,1H), 3.70 (s,3H), 4.86 (dd,1H), 4.97 (d,1H), 5.2 (d,1H), 5.3 (s,1H), 6.13 (d,1H).

EXAMPLE 154

Cbz-[(β,β-di-Me)-β-Ala]-Phe-OH

To a 0° C. solution of Cbz-[(β,β-di Me)-β-Ala]-Phe-OMe (1.5 g, 3.63 mmol) in dioxane (15 mL) was added a solution of lithium hydroxide (0.174 g, 4.15 mmol) in water (7.5 mL). After stirring for 1 h at 0°-5° C., the reaction mixture was diluted with cold water and extracted 2× with ether. The aqueous portion was acidified with 6N HCl and extracted with ether. The organic extract was washed with brine and evaporated to give an 87% yield of product as a viscous liquid.

EXAMPLE 155

Cbz-[(β,β-di-Me)-β-Ala]-Phe-His Amide of 2-Amino-1-cyclohexyl-3-hydroxy-6-methylheptane Following the procedure of Example 145, but replacing Cbz-D-Ala-Phe-OH with the resultant compound of Example 154 gave the desired product.

EXAMPLE 156

H-[(β,β-di-Me)-β-Ala]-Phe-His Amide of 2-Amino-1-cyclohexyl-3-hydroxy-6-methylheptane Following the procedure of Example 146, but replacing the resultant compound of Example 145 with the resultant cmpound of Example 155, gave the desired product.

EXAMPLE 157

3-Benzyloxycarbonylamino-2,2-dimethylpropionic Acid

3-Carbomethoxy-3-methylbutanoic acid [Bull. Soc. Chim. Fr., 828 (1965), 7.85 g, 0.049 mol] was reacted with diphenylphosphorylazide and triethylamine as described in Example 36. After heating the toluene solution for 1.5 h, benzyl alcohol (8 g) was added directly to the reaction mixture and heating at reflux was continued for 20 h. Work-up and chromatography gave methyl 3-benzyloxycarbonylamino-2,2-dimethylpropionate. NMR (300 MHz, CDCl$_3$): 1.2 (s,6H), 3.3 (d,2H), 3.68 (s,3H), 5.1 (s,2H), 5.22 (m,1H). A sample of the methyl ester (6.21 g, 0.023 mol) was saponified with 3.1 g (0.78 mol) of NaOH in 100 mL ethanol/10 mL H$_2$O at room temperature for 48 h. Work-up as in Example 36 gave the desired product as a liquid. NMR (300 MHz, CDCl$_3$): 1.23 (s,6H), 3.32 (d,2H), 5.10 (s,2H), 5.27 (m,1H).

EXAMPLE 158

Cbz-[(α,α-di-Me)-β-Ala](OMe)Tyr-OCH$_3$

To a solution of 3 benzyloxycarbonylamino-2,2-dimethylpropionic acid (1.5 g, 5.97 mmol) in methylene chloride (13 mL) was added oxalyl chloride (0.757 g, 5.97 mmol) and dimethylformamide (30 uL). After stirring for 1 h at room temperature, the reaction mixture was cooled to 0° C. and treated successively with OMe-tyrosine methyl ester hydrochloride (1.465 g, 5.97 mmol) and N-methylmorpholine (1.81 g, 17.9 mmol). Stirring for 1 h at 0°–5° C. was followed by distribution between CH$_2$Cl$_2$ and 0.5 N HCl. The organic phase was washed with aqueous NaHCO$_3$ and brine and dried over MgSO$_4$. Evaporation of the solvent gave a residue which was purified by chromatography. There was obtained a 61.5% yield of product as a liquid.

EXAMPLE 159

Cbz-[(α,α-di-Me)-β-Ala]-(OMe)Tyr-OH

To a 0° C. solution of Cbz-[(α,α-di-Me)-β-Ala]-(OMe)-Tyr-OMe (1.2 g, 2.71 mmol) in dioxane (15 mL) was added a solution of lithium hydroxide (0.115 g, 2.75 mmol) in water (7.5 mL). After stirring for 1 h at 0°–5° C., the reaction mixture was diluted with cold water and extracted 2× with ether. The aqueous portion was acidified with 6N HCl and extracted with ether. The organic extract was washed with brine and evaporated to give an 87% yield of product as a viscous liquid.

EXAMPLE 160

Cbz-[(α,α-di Me)-β-Ala]-(OMe)Tyr-His Amide of 2-Amino-1-cyclohexyl-3-hydroxy-6-methylheptane Following the procedure of Example 145, but replacing Cbz-D-Ala-Phe-OH with the resultant compound of Example 159, gave the desired product.

EXAMPLE 161

H-[(α,α-di-Me)-β-Ala]-(OMe)Tyr-His Amide of 2-Amino-1-cyclohexyl-3-hydroxy-6-methylheptane Following the procedure of Example 146, but replacing the resultant compound of Example 145 with the resultant compound of Example 160, gave the desired product.

EXAMPLE 162

2(S)-[[(4-Morpholinyl)carbonyl]oxy]-3-phenylpropionic Acid Methyl Ester

To L-phenyllactic acid methyl ester (3.2 g) was added 150 mL of 12.5% phosgene in toluene and 25 drops of dimethylformamide. After stirring for 16 h at room temperature, the solvent was evaporated and the residue chased several times with benzene. The resulting product was dissolved in methylene chloride (50 mL), cooled to 0° C. and treated by dropwise addition with 3.86 g (0.044 mol) of morpholine. The reaction mixture was stirred for 2 h at 0°–5° C. and then distributed between 0.5N HCl and methylene chloride. The organic phase was washed with aqueous NaHCO$_3$ and brine and evaporated to a residue. Flash chromatography on silica gel eluting with 2/1 ether-hexane gave a 65% yield of product. NMR (300 MHz): 3.08 (dd,1H), 3.20 (dd,1H), 3.8 (s,3H), 5.19 (dd,1H).

EXAMPLE 163

2(S)-[(4-Morpholinyl)carbonyl]oxy-3-phenylpropionic Acid

Using the hydrolysis procedure of Example 159, the title compound was obtained in 90% yield.

EXAMPLE 164

2(S)-[(4-Morpholinyl)carbonyl]oxy-3 phenylpropionyl-His Amide of 2-Amino-1-cyclohexyl-3-hydroxy-6-methylheptane Following the procedure of Example 145, but replacing Cbz-D-Ala-Phe-OH with the resultant compound of Example 163, gave the desired product.

EXAMPLE 165

(3,4-cis-dihydroxypyrrolidinylcarbonyl)-Phe-methyl Ester

A suspension of L-phenylalamine methyl ester hydrochloride (10 g) in toluene (200 mL) was heated to 100° C. while phosgene gas was bubbled into the reaction mixture. After approximately 2 h the mixture became homogeneous. The bubbling of phosgene was continued for 15 more minutes keeping the temperature at 100° C. The toluene was then evaporated and the residue chased with benzene several times. The isocyanate from L-Phe-OCH$_3$ was then dissolved in 100 mL of methylene chloride and 1.1 equivalent of 3-pyrroline (75% pure) was added dropwise at 0° C. After 15 min, the reaction mixture was washed with 0.5N HCl and methylene chloride. The organic layer was washed with aqueous NaHCO₃ and dried over MgSO₄. Evaporation of the solvent gave 3-pyrrolinylcarbonyl-Phe-methyl ester which was cis-hydroxylated under the following conditions: 2.5 g of the 3-pyrrolinylcarbonyl-Phe-methyl ester was dissolved in 50 mL of THF and 5 mL of a 2 5% solution of OsO₄ in t-butanol was added, followed by 1.15 g of N methylmorpholine-N-oxide. After 1 h, the solvent was evaporated and the residue dissolved in 150 mL of ethyl acetate and washed with dilute Na₂SO₃ solution, satd. NaHCO₃ solution and then dried with MgSO₄. Evaporation of the solvent gave a gummy solid which was purified by SiO₂ column chromatography (5% MeOH/CH₂Cl₂) to give the desired compound (65% yield). Mass spectrum: $M^+ = 308$.

EXAMPLE 166

(3,4-cis-dihydroxycyrrolidinylcarbonyl)-Phe-OH

Using the procedure of Example 159 and replacing Boc-Sta-OEt with the compound from Example 165 gave the desired compound. Mass spectrum: $M^+ = 294$.

EXAMPLE 167

(3,4-cis-dihydroxypyrrolidinylcarbonyl)-Phe-His Amide of 2-Amino-1-cyclohexyl-3-hydroxy-6 methylheptane Following the procedure of Example 145, but replacing Cbz-D Ala-Phe-OH with the resultant compound of Example 166, gave the desired product.

The compounds of the present invention can be used in the form of salts derived from inorganic or organic acids. Included among such salts are the following: acetate, adipate, alginate, aspartate, benzoate, benzenesulfonate, bisulfate, butyrate, citrate, camphorate, camphorsulfonate, dodecylsulfate, cyclopentanepropionate, digluconate, ethanesulfonate, fumarate, glucoheptanoate, glycerophosphate, hexanoate, hemisulfate, heptonate, hydrochloride, hydrobromide, hydroiodide, 2-hydroxyethanesulfonate, lactate, maleate, methanesulfonate, 2-naphthalenesulfonate, nicotinate, oxalate, pamoate, pectinate, persulfate, 3-phenylpropionate, picrate, pivalate, propionate, succinate, tartrate, thiocyanate, tosylate, and undecanoate. Also, the basic nitrogen-containing groups can be quaternized with such agents as loweralkyl halides, such as methyl, ethyl, propyl and butyl chloride, bromides and iodides; dialkyl sulfates like dimethyl, diethyl, dibutyl; and diamyl sulfates, long chain halides such as decyl, lauryl, myristyl and stearyl chlorides, bromides and iodides, aralkyl halides like benzyl and phenethyl bromides and others. Water or oil soluble or dispersible products are thereby obtained.

The novel compounds of the present invention possess an excellent degree of activity and specificity in treating renin associated hypertension in a host. The ability of the compounds of the invention to inhibit human renal renin can be demonstrated in vitro by reacting a selected compound at varied concentrations with human renal renin, free from acid proteolytic activity, and with human renin substrate (angiotensinogen) at 37° C. and pH 6.0. At the end of the incubation, the amount of angiotensin I formed is measured by radioimmunoassay and the percent inhibition or renin is calculated. When tested in accordance with the foregoing procedure, the compounds of the invention demonstrated a high level of enzyme inhibition as shown on Table I.

TABLE I

| Compounds (Example No.) | Inhibition |
|---|---|
| Example 23 | 56% @ $10^{-6}$ |
| Example 25 | 56% @ $10^{-5}$ |
| Example 28 | 57% @ $10^{-5}$ |
| Example 29 | 94% @ $10^{-5}$ |
| Example 31 | 31% @ $10^{-5}$ |
| Example 50 | 89% @ $10^{-7}$ |
| Example 51 | 80% @ $10^{-8}$ |
| Example 54 | 81% @ $10^{-8}$ |
| Example 55 | 46% @ $10^{-5}$ |
| Example 79 | 63% @ $10^{-6}$ |
| Example 81 | 71% @ $10^{-7}$ |
| Example 82 | 82% @ $10^{-8}$ |

Total daily dose administered to a host in single or divided doses may be in amounts, for example, from 0.001 to 10 mg/kg body weight daily and more usually 0.01 to 1 mg. Dosage unit compositions may contain such amounts or submultiples thereof to make up the daily dose.

The amount of active ingredient that may be combined with the carrier materials to produce a single dosage form will vary depending upon the host treated and the particular mode of administration.

It will be understood, however, that the specific dose level for any particular patient will depend upon a variety of factors including the activity of the specific compound employed, the age, body weight, general health, sex, diet, time of administration, route of administration, rate of excretion, drug combination and the severity of the particular disease undergoing therapy.

The compounds of the present invention may be administered orally, parenterally, by inhalation spray, rectally or topically in dosage unit formulations containing conventional nontoxic pharmaceutically acceptable carriers, adjuvants and vehicles as desired. The term parenteral as used herein includes subcutaneous injections, intravenous, intramuscular, intrasternal injection or infusion techniques.

Injectable preparation, for example, sterile injectable aqueous or oleagenous suspensions may be formulated according to the known art using suitable dispersing or wetting agents and suspending agents. The sterile injectable preparation may also be a sterile injectable solution or suspension in a nontoxic parenterally acceptable diluent or solvent, for example, as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectibles.

Suppositories for rectal administation of the drug can be prepared by mixing the drug with a suitable nonirritating excipient such as cocoa butter and polyethylene glycols which are solid at ordinary temperatures but liquid at the rectal temperature and will therefor melt in the rectum and release the drug.

Solid dosage forms for oral administration may include capsules, tablets, pills, powders and granules. In such solid dosage forms, the active compound may be admixed with at least one inert diluent such as sucrose, lactose or starch. Such dosage forms may also comprise, as is normal practice, additional substances other than inert diluents, e.g., lubricating agents such as magnesium stearate. In the case of capsules, tablets and pills, the dosage forms may also comprise buffering agents. Tablets and pills can additionally be prepared with enteric coatings.

Liquid dosage forms for oral administration may include pharmaceutically acceptable emulsions, solutions, suspensions, syrups and elixirs containing inert diluents commonly used in the art, such as water. Such compositions may also comprise adjuvants, such as wetting agents, emulsifying and suspending agents, and sweetening, flavoring and perfuming agents.

The foregoing is merely illustrative of the invention and is not intended to limit the invention to the disclosed compounds. Variations and changes which are obvious to one skilled in the art are intended to be within the scope and nature of the invention which are defined in the appended claims.

We claim:

1. A compound of the formula:

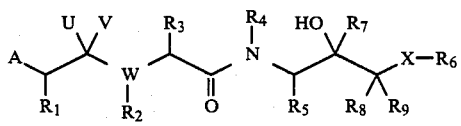

wherein A is hydrogen; $C_1$-$C_6$ loweralkyl; arylalkyl; $OR_{10}$ wherein $R_{10}$ is hydrogen or $C_1$-$C_6$ loweralkyl; $NR_{11}R_{12}$ wherein $R_{11}$ is hydrogen or $C_1$-$C_6$ loweralkyl and $R_{12}$ is hydrogen or $C_1$-$C_6$ loweralkyl; or $R_{13}$—CO—B wherein B is NH, O, $CH_2$, or $HNCH_2$ and $R_{13}$ is $C_1$-$C_6$ loweralkyl, alkoxy, arylalkoxy, arylalkoxyalkyl, amino, alkylamino, dialkylamino, aminoalkyl, N-protected aminoalkyl, hydroxylated dialkylamino, (heterocyclic)alkyl or a substituted or unsubstituted heterocyclic having one to three heteroatoms selected from the group consisting of nitrogen, oxygen and sulfur, carboxyalkyl or $C_1$-$C_6$ lower alkyl carboxyalkyl esters; W is N or CH; U,V is H,OH; OH,H; or H,H; or when taken together as O is a carbonyl group with the provisos that when U,V is H,OH, or OH,H tyhen W is CH, and when U,V is O then W is N; $R_1$ is $C_1$-$C_6$ loweralkyl, benzyl, beta-naphthylmethyl or 4-methoxybenzyl, $R_3$ is $C_1$-$C_6$ loweralkyl, hydroxy substituted $C_1$-$C_6$ loweralkyl, benzyl, 4-hydroxybenzyl or 4-imidazolylmethyl, $R_5$ is $C_1$-$C_6$ loweralkyl or cycloalkyl methyl; $R_2$, $R_4$, $R_7$, $R_8$ and $R_9$ are independently selected from the group consisting of hydrogen and $C_1$-$C_6$ loweralkyl; X is NH, O, S, SO, $SO_2$, or $CH_2$; and $R_6$ is $C_1$-$C_6$ loweralkyl, cycloalkyl, cycloalkylalkyl, aryl, arylalkyl or an N-protecting group, with the proviso that $R_6$ is an N-protecting group only when X is NH.

2. A compound of claim 1 wherein $R_1$ and $R_5$ are benzyl, beta-naphthylmethyl or 4-methoxybenzyl in the definition of $R_1$ and cycloalkyl methyl for R5.

3. A compound of claim 2 wherein $R_2$, $R_4$, $R_7$, $R_8$ and $R_9$ are hydrogen.

4. A compound of claim 3 wherein $R_1$ is benzyl or betanaphthylmethyl.

5. A compound of claim 4 wherein $R_3$ is methyl.

6. A compound of claim 4 wherein $R_3$ is imidazol-4-yl-methyl.

7. A compound of claim 4 wherein $R_5$ is isobutyl.

8. A compound of claim 4 wherein $R_5$ is cyclohexylmethyl.

9. A compound of claim 4 wherein X is S or $SO_2$.

10. A compound of claim 4 wherein $R_6$ is cyclohexyl or isopropyl.

11. A compound of claim 4 wherein X is oxygen.

12. A compound of claim 4 wherein X is NH.

13. A compound of claim 3 wherein X is S, $R_1$ is benzyl, $R_3$ is imidazole-4-yl-methyl, $R_5$ is cyclohexylmethyl and $R_6$ is isopropyl or cyclohexyl.

14. A compound of claim 3 wherein X is S, $R_1$ is β-naphthylmethyl, $R_3$ is imidazole-4-yl-methyl, $R_5$ is cyclohexylmethyl or isobutyl and $R_6$ is cyclohexyl.

15. A compound of claim 3 wherein X is $SO_2$, $R_1$ is benzyl, $R_3$ is imidazole-4-yl-methyl, $R_5$ is cyclohexylmethyl and $R_6$ is cyclohexyl or isopropyl.

16. A pharmaceutical composition for treating hypertension, comprising a pharmaceutical carrier and a therapeutically effective amount of a compound of claim 1.

17. A method of treating hypertension comprising administering to a host a therapeutically effective amount of a compound of claim 1.

* * * * *

UNITED STATES PATENT AND TRADEMARK OFFICE
CERTIFICATE OF CORRECTION

PATENT NO. : 4,826,815

DATED : May 2, 1989

INVENTOR(S) : Jay R. Luly, et al.

It is certified that error appears in the above-identified patent and that said Letters Patent is hereby corrected as shown below:

Title page, before patent date insert an asterisk (*).

Title page, column 1, TERMINAL DISCLAIMER should be inserted after item [73]:

[*] Notice: --The portion of the term of this patent subsequent to February 24, 2004 has been disclaimed.--

Column 37, line 40: Replace "tyhen" with --then--.

Column 38, line 9: Replace "and $R_5$ are" with --is--.

Column 38, lines 10-11: Delete "in the definition of $R_1$".

Column 38, line 11: Replace "cycloalkyl methyl for $R_5$" with --$R_5$ is cycloalkylmethyl--.

Signed and Sealed this

Fourteenth Day of May, 1991

Attest:

HARRY F. MANBECK, JR.

Attesting Officer

Commissioner of Patents and Trademarks